United States Patent [19]
Schneider et al.

[11] Patent Number: 5,965,510
[45] Date of Patent: *Oct. 12, 1999

[54] ENHANCEMENT OF ENZYME REACTIONS

[75] Inventors: Palle Schneider, Ballerup; Søren Ebdrup, Copenhagen, both of Denmark

[73] Assignee: Novo Nordisk A/S, Bagaværd, Denmark

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/436,315

[22] PCT Filed: Dec. 1, 1993

[86] PCT No.: PCT/DK93/00395

§ 371 Date: May 12, 1995

§ 102(e) Date: May 12, 1995

[87] PCT Pub. No.: WO94/12621

PCT Pub. Date: Jun. 9, 1994

[30] Foreign Application Priority Data

| Dec. 1, 1992 | [DK] | Denmark | 1441/92 |
| Jun. 29, 1993 | [DK] | Denmark | 772/93 |
| Oct. 25, 1993 | [DK] | Denmark | 1197/93 |
| Oct. 26, 1993 | [DK] | Denmark | 1200/93 |

[51] Int. Cl.⁶ .......................... C11D 3/386; C11D 3/395; D06L 3/00
[52] U.S. Cl. .......................... 510/397; 510/305; 510/306; 510/374; 510/375; 8/157
[58] Field of Search .......................... 252/95, 102, 174.12, 252/DIG. 12; 435/192; 510/30, 392, 374, 375, 320, 321, 305, 306; 8/137

[56] References Cited

U.S. PATENT DOCUMENTS

| 3,893,803 | 7/1975 | Kaiser | 8/10.2 |
| 4,318,984 | 3/1982 | Magers et al. | 435/14 |
| 4,432,921 | 2/1984 | Haars et al. | 264/109 |
| 4,623,465 | 11/1986 | Klibanov | 210/632 |
| 4,690,895 | 9/1987 | Farrell | 435/278 |
| 5,445,755 | 8/1995 | Convetls et al. | 252/102 |
| 5,451,337 | 9/1995 | Liu et al. | 252/102 |
| 5,610,129 | 3/1997 | McCorquodale et al. | 510/320 |
| 5,700,769 | 12/1997 | Schneider et al. | 510/305 |

FOREIGN PATENT DOCUMENTS

| 0 179 486 | 10/1985 | European Pat. Off. . |
| 0 361 470 A2 | 9/1989 | European Pat. Off. . |
| 0361470 | 4/1990 | European Pat. Off. . |
| WO 91/05839 | 5/1991 | WIPO . |
| WO 92/18683 | 10/1992 | WIPO . |
| WO 92/18687 | 10/1992 | WIPO . |

OTHER PUBLICATIONS

Abstract of DD 147368.
Bourbonnais et al., FEBS 08563, vol. 267, No. 1, pp. 99–102 (Jul. 1990).
Bourbonnais et al., Appl Microbiol Biotechnol, vol. 36, pp. 823–27 (1992).

(List continued on next page.)

*Primary Examiner*—Kery Fries
*Attorney, Agent, or Firm*—Steve T. Zelson, Esq.; Elias J. Lambiris, Esq.

[57] ABSTRACT

This invention relates to activation of enzymes. More specifically, the invention relates to agents capable of enhancing the activity of peroxidases or peroxidase acting compounds. The invention also relates to methods of oxidizing a substrate with a source of hydrogen peroxide in the presence of a peroxidase enzyme or a peroxidase acting compound, and an enhancing agent. More specifically, the invention relates to a method of bleaching of dye in solutions, to a method of inhibiting the transfer of a textile dye from a dyed fabric to another fabric when said fabrics are washed together in a wash liquor, to a method of bleaching of lignin-containing material, in particular bleaching of pulp for paper production, to a method of treatment of waste water from pulp manufacturing, and to a method of enzymatic polymerization and/or modification of lignin or lignin containing material.

34 Claims, 10 Drawing Sheets

OTHER PUBLICATIONS

Kato et al., Plant Cell Physiol, vol. 26, No.7, pp. 1291–301 (1985).

Charkraborty et al., Indian Journal of Biochemistry & Biophysics, vol.24, pp. 81–86, Apr. 1987.

Schramm et al., Biochemical Pharmacology, vol.34, No. 20, pp. 3735–3739, 1985.

Sanchez et al., Physiologia Plantarum, vol. 75:275–279, 1989.

Kenten et al., Coupled Oxidations Involving Peroxidase, pp. 141–215.

(I)

(II)

(III)

(IV)

(V)

(VI)

(VII)

(VIII)

(IX)

(X)

(XI)

(XII)

(XIII)

(XIV)

(XV)

(XVI)

(XVII)

(XVIII)

(XIX)

(XX)

(XXI)

(XXII)

ENHANCEMENT OF ENZYME REACTIONS

CROSS-REFERENCE TO RELATED APPLICATIONS

This application is a 371 of PCT/DK93/00395 filed Dec. 1, 1993, which is incorporated herein by reference.

TECHNICAL FIELD

This invention relates to activation of enzymes. More specifically, the invention relates to agents capable of enhancing the activity of peroxidases or peroxidase acting compounds.

The invention also relates to methods of oxidizing a substrate with a source of hydrogen peroxide in the presence of a peroxidase enzyme or a peroxidase acting compound, and an enhancing agent. More specifically, the invention relates to a method of bleaching of dye in solutions, to a method of inhibiting the transfer of a textile dye from a dyed fabric to another fabric when said fabrics are washed together in a wash liquor, to a method of bleaching lignin-containing material, in particular bleaching of pulp for paper production, to a method of treatment of waste water from pulp manufacturing, and to a method of enzymatic polymerization and/or modification of lignin or lignin containing material.

BACKGROUND ART

Peroxidases (E.C. 1.11.1.7) are enzymes that catalyse the oxidation of a substrate (an electron or hydrogen donor) with hydrogen peroxide. Such enzymes are known from microbial, plant and animal origins, e.g. peroxidase from *Coprinus cinereus* (cf. e.g. EP 179,486). They are typically hemoproteins, i.e. they contain a heme as a prosthetic group.

Use of peroxidase together with hydrogen peroxide or a hydrogen peroxide precursor has been suggested e.g. in bleaching of pulp for paper production, in treatment of waste water from pulp production, for improved bleaching in laundry detergents, for dye transfer inhibition during laundering, and for lignin modification, e.g. in particle board production.

The compound 2,2'-azino-bis(3-ethylbenzothiazoline-6-sulfonate), ABTS, supplied by Boehringer Mannheim, is a chromogenic substrate, and a common peroxidase and phenol oxidase assay agent. These enzymes catalyse the oxidation of ABTS by hydrogen peroxide and dioxygen, respectively, producing a greenish-blue colour, which process may be monitored photometrically.

ABTS has been found to form a stable radical cation when oxidized by a laccase enzyme (polyphenol oxidase, EC 1.10.3.2), and has been proposed to act as a redox mediator for oxidation of non-phenolic lignin model compounds [Bourbonnais R. Paice M G; FEBS Lett (1990) 267 99–102].

Studies on demethylation and delignification of kraft pulp by a laccase enzyme in the presence of ABTS showed that the extent of partial demethylation by laccase was increased in the presence of ABTS [Bourbonnais, R. and Paice, M. G; Appl. Microbiol. Biotechnol. (1992) 36 823–827].

Certain oxidizable substrates e.g. metal ions and phenolic compounds such as 7-hydroxycoumarin (7HCm), vanillin (VAN), and p-hydroxybenzenesulfonate (pHBS), have been described as accelerators or enhancers, able to enhance bleaching reactions (cf. e.g. WO 92/18683, WO 92/18687, and Kato M and Shimizu S, Plant Cell Physiol. 1985 26 (7), pp. 1291–1301 (cf. Table 1 in particular), or Saunders B C, et al., Peroxidase, London, 1964, p. 141 ff).

SUMMARY OF THE INVENTION

It has now surprisingly been found that organic chemical compounds consisting of at least two aromatic rings, of which aromatic rings at least one ring is substituted with one or more of the following atoms: nitrogen, oxygen, and sulfur, and which aromatic rings may furthermore be fused rings, are capable of enhancing the activity of peroxidases and peroxidase acting compounds.

Accordingly, in its first aspect, the invention provides an agent for enhancing the activity of peroxidases or peroxidase acting compounds, which agent is an organic chemical compound consisting of at least two aromatic rings, of which aromatic rings at least one ring is substituted with one or more of the following atoms: nitrogen, oxygen, and sulfur; and which aromatic rings may furthermore be fused rings.

In a more specific aspect, the invention provides an agent for enhancing the activity of peroxidases or peroxidase acting compounds, which agent is an organic chemical compound of the general formula I:

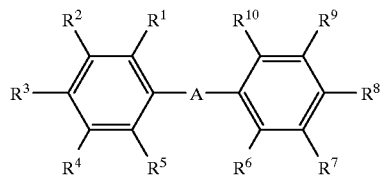

in which general formula A represents a single bond, or one of the following groups: $(-CR^{11}=CR^{15}-)_n$, $(-NR^{11}-)$, $(-CR^{11}=N-)_n$, $(-NR^{11}-CR^{12}=N-N=CR^{13}-NR^{15}-)$, $(-NR^{11}-CR^{12}=N-N=CR^{15}-)$, $(-NR^{11}-CR^{12}=N-)_n$, $(-CR^{12}=N-NR^{11}-)$, $(-NR^{11}-CR^{12}=CR^{13}-)$, $(-N=N-)$, in which groups n represents an integer of from 1 to 6; or A represents carbon, carbonyl, nitrogen, sulfur, oxygen, selenium, or phosphor, which carbon, phosphor and nitrogen may be unsubstituted or substituted with a substituent group $R^{11}$;

and in which general formula the substituent groups $R^1$–$R^{13}$ and $R^{15}$, which may be identical or different, independently represents any of the following radicals: hydrogen, halogen, hydroxy, formyl, carboxy and esters and salts hereof, carbamoyl, sulfo and esters and salts hereof, sulfamoyl, phospho, phosphono, phosphonooxy, sulfandiyl, nitro, amino, phenyl, $C_1$–$C_{14}$-alkyl, $C_1$–$C_5$-alkoxy, carbonyl-$C_1$–$C_5$-alkyl, aryl-$C_1$–$C_5$-alkyl; which carbamoyl, sulfamoyl, and amino groups may furthermore be unsubstituted or substituted once or twice with a substituent group $R^{14}$; and which phenyl may furthermore be unsubstituted or substituted with one or more substituent groups $R^{14}$; and which $C_1$–$C_{14}$-alkyl, $C_1$–$C_5$-alkoxy, carbonyl-$C_1$–$C_5$-alkyl, and aryl-$C_1$–$C_5$-alkyl groups may be saturated or unsaturated, branched or unbranched, and may furthermore be unsubstituted or substituted with one or more substituent groups $R^{14}$;

which substituent group $R^{14}$ represents any of the following radicals: halogen, hydroxy, formyl, carboxy and esters and salts hereof, carbamoyl, sulfo and esters and salts hereof, sulfamoyl, nitro, amino, phenyl, aminoalkyl, piperidino, piperazinyl, pyrrolidino, $C_1$–$C_5$-alkyl, $C_1$–$C_5$-alkoxy; which carbamoyl, sulfamoyl, and amino groups may furthermore be unsubstituted or substituted once or twice with hydroxy, $C_1$–$C_5$-alkyl, $C_1$–$C_5$-alkoxy; and which phenyl may furthermore be substituted with one or more of the following radicals: halogen, hydroxy, amino, formyl, carboxy and esters and salts hereof, carbamoyl, sulfo and esters and salts hereof, and sulfamoyl; and which $C_1$–$C_5$-alkyl, and $C_1$–$C_5$-alkoxy groups may furthermore be saturated or unsaturated, branched or unbranched, and may furthermore be substituted once or twice with any of the following radicals: halogen, hydroxy, amino, formyl, carboxy and esters and salts hereof, carbamoyl, sulfo and esters and salts hereof, and sulfamoyl;

or in which general formula $R^5$ and $R^6$ may together form a group —B—, in which B represents a single bond, the group (—CH═CH—)$_n$, or the group (—CH═N—)$_n$, in which groups n represents an integer of from 1 to 6; or B represents carbon, nitrogen, sulfur, oxygen, selenium, or tellurium, which carbon and nitrogen may be unsubstituted or substituted with a substituent group $R^{14}$ as defined above;

or in which general formula two of the substituent groups $R^1$–$R^{10}$ may together form a group —C—, in which C represents any of the following groups: (—CHR$^{11}$—N═N—), (—CH═CH—)$_n$, (—CH═N—)$_n$, in which groups n represents an integer of from 2 to 4, and in which groups $R^{11}$ is a substituent group as defined above;

or in which general formula $R^5$ and $R^{12}$, and/or $R^6$ and $R^{13}$, when n in the above formula being 1, may together form a group —D—, in which D represents the groups: (—CHR$^{11}$—), (—NR$^{11}$—), (—CR$^{11}$═CR$^{15}$—), (—CR$^{11}$═N—), (—N═CR$^{11}$—), (—O—), (>C═O) or (—S—), and in which groups $R^{11}$ and $R^{15}$ are substituent groups as defined above.

In another specific aspect, the invention provides an agent for enhancing the activity of peroxidases or peroxidase acting compounds, which agent is an organic chemical compound of the general formula II:

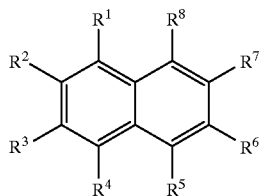

in which the substituent groups $R^1$–$R^8$, which may be identical or different, independently represents any of the following radicals: hydrogen, halogen, hydroxy, formyl, carboxy and esters and salts hereof, carbamoyl, sulfo and esters and salts hereof, sulfamoyl, nitro, amino, phenyl, $C_1$–$C_{14}$-alkyl, $C_1$–$C_5$-alkoxy, carbonyl-$C_1$–$C_5$-alkyl, aryl-$C_1$–$C_5$-alkyl; which carbamoyl, sulfamoyl, and amino groups may furthermore be unsubstituted or substituted once or twice with a substituent group $R^9$; and which phenyl may furthermore be unsubstituted or substituted with one or more substituent groups $R^9$; and which $C_1$–$C_{14}$-alkyl, $C_1$–$C_5$-alkoxy, carbonyl-$C_1$–$C_5$-alkyl, and aryl-$C_1$–$C_5$-alkyl groups may be saturated or unsaturated, branched or unbranched, and may furthermore be unsubstituted or substituted with one or more substituent groups $R^9$;

which substituent group $R^9$ represents any of the following radicals: halogen, hydroxy, formyl, carboxy and esters and salts hereof, carbamoyl, sulfo and esters and salts hereof, sulfamoyl, nitro, amino, phenyl, $C_1$–$C_5$-alkyl, $C_1$–$C_5$-alkoxy; which carbamoyl, sulfamoyl, and amino groups may furthermore be unsubstituted or substituted once or twice with hydroxy, $C_1$–$C_3$-alkyl, $C_1$–$C_3$-alkoxy; and which phenyl may furthermore be substituted with one or more of the following radicals: halogen, hydroxy, amino, formyl, carboxy and esters and salts hereof, carbamoyl, sulfo and esters and salts hereof, and sulfamoyl; and which $C_1$–$C_5$-alkyl, and $C_1$–$C_5$-alkoxy groups may furthermore be saturated or unsaturated, branched or unbranched, and may furthermore be substituted once or twice with any of the following radicals: halogen, hydroxy, amino, formyl, carboxy and esters and salts hereof, carbamoyl, sulfo and esters and salts hereof, and sulfamoyl;

or in which general formula two of the substituent groups $R^1$–$R^8$ may together form a group —B—, in which B represents any of the following groups: (—N═N—), (—CH═CH—)$_n$, (—CH═N—)$_n$, (—N═CR$^9$—NR$^{10}$—) or (—N═N—CR$^9$—), in which groups n represents an integer of from 1 to 3, $R^9$ is a substituent group as defined above and $R^{10}$ is defined as $R^9$.

In another aspect, the invention provides a method for oxidizing a substrate with a peroxidase or a peroxidase acting compound, in the presence of a source of hydrogen peroxide, in the presence of an enhancing agent of the invention.

In a more specific aspect, the invention provides a method for bleaching dye in solutions by treatment with a peroxidase enzyme or a peroxidase acting compound in the presence of a source of hydrogen peroxide in the presence of an enhancing agent of the invention.

In another specific aspect, the invention provides a method of inhibiting the transfer of a textile dye from a dyed fabric to another fabric when said fabrics are washed together in a wash liquor, the method comprising treatment of the wash liquor with a peroxidase or peroxidase acting compound in the presence of a source of hydrogen peroxide and in the presence of an enhancing agent of the invention.

In another aspect, the invention provides a method of bleaching lignin-containing material, in particular bleaching of pulp for paper production, the method comprising treatment of the lignin or lignin containing material with a peroxidase or a peroxidase acting compound in the presence of a source of hydrogen peroxide and in the presence of an enhancing agent of the invention.

In a further aspect, the invention provides a method of enzymatic polymerization and/or modification of lignin or lignin containing material, the method comprising treatment of the lignin or lignin containing material with a peroxidase or a peroxidase acting compound in the presence of a source of hydrogen peroxide and in the presence of an enhancing agent of the invention.

In a yet further aspect, the invention provides a method of treatment of waste water, in particular waste water from pharmaceutical or chemical industry, e.g. waste water from dye manufacturing, from textile industry, or from pulp manufacturing, the method comprising treatment of the waste water with a peroxidase or a peroxidase acting compound in the presence of a source of hydrogen peroxide and in the presence of an enhancing agent of the invention.

In a particular aspect, the invention provides a detergent additive capable of inhibiting the transfer of a textile dye from a dyed fabric to another fabric when said fabrics are washed together in a wash liquor, the detergent additive comprising an enzyme exhibiting peroxidase activity or a peroxidase acting compound, a source of hydrogen peroxide and an enhancing agent of the invention.

In other aspects, the invention provides detergent additives and detergent compositions capable of inhibiting the transfer of a textile dye from a dyed fabric to another fabric when said fabrics are washed together in a wash liquor, the detergent composition comprising an enzyme exhibiting peroxidase activity or a peroxidase acting compound, a source of hydrogen peroxide, and an enhancing agent of the invention.

BRIEF DESCRIPTION OF DRAWINGS

The present invention is further illustrated by reference to the accompanying drawings, in which.

Figure 1A:
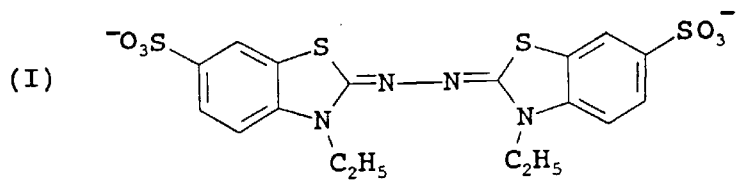
FIG. 1 shows the specific formulas of some enhancing agents of the invention (I) 2,2'-azino-bis (3-ethylbenzothiazoline-6-sulfonate (ABTS); (II) 6-hydroxy-2-naphtoic acid; (III) 6-bromo-2-naphtol; (IV) 7-methoxy-2-naphtol; (V) 7-amino-2-naphthalene sulfonic acid; (VI) 5-amino-2-naphthalene sulfonic acid; (VII) 1,5-diaminonaphthalene; (VIII) 7-hydroxy-1,2-naphthimidazole; (IX) 10-methylphenothiazine; (X) 10-phenothiazine-propionic acid; (XI) N-hydroxysuccinimide- 10-phenothiazine-propionate; (XII) benzidine; (XIII) 3,3'-dimethylbenzidine; (XIV) 3,3'-dimethoxybenzidine; (XV) 3,3',5,5'-tetramethylbenzidine; (XVI) 4'-hydroxy-4-biphenylcarboxylic acid; (XVII) 4-amino-4'-methoxystilbene; (XVIII) 4,4'-diaminostilbene-2,2'-disulfonic acid; (XIX) 4,4'-diaminodiphenylamine, (XX) 2,7-diaminofluorene; (XXI) 4,4'-dihydroxy-biphenylene; (XXII) triphenylamine); (XXIII) 10-ethyl-4-phenothiazinecarboxylic acid; (XXIV) 10-ethylphenothiazine; (XXV) 10-propylphenothiazine; (XXVI) 10-isopropylphenothiazine; (XXVII) methyl-10-phenothiazinepropionate; (XXVIII) 10-phenylphenothiazine; (XXIX) 10-allylphenothiazine; (XXX) 2-chloro-10-methylphenothiazine; (XXXI) 10-(3-(4-methyl-1-piperazinyl)propyl)phenothiazine; (XXXII) 10-(2-pyrrolidinoethyl)phenothiazine; (XXXIII) chlorpromazine; (XXXIV) 10-methylphenoxazine; (XXXV) 6-amino-3-methyl-2-benzothiazolinone azine with 3-methyl-2-benzothiazolinone; (XXXVII) iminostilbene; (XXXVIII) 2-(p-aminophenyl)-6-methylbenzothiazole-7-sulfonic acid; (XXXIX) N-benzylidene-4-biphenylamine; (XL) 4,4'-diaminodiphenylaminesulfate; (XLI) 5-amino-2-naphthalenesulfonic acid; (XLII) 1,6-dibromo-2-naphtol; (XLIII) 7-methoxy-2-naphtol; (XLIV) 4,4'-dihydroxybenzophenone; (XLV) N-(4-(dimethylamino) benzylidene)p-anisidine; (XLVI) 3-methyl-2-benzothiazolinone(4-(dimethylamino)benzylidene) hydrazone; (XLVII) 2-acethyl-10-methylphenothiazine.
Figure 1A:
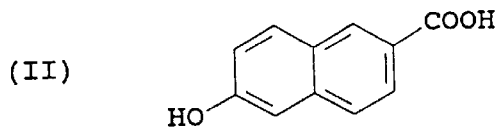
Figure 1A:
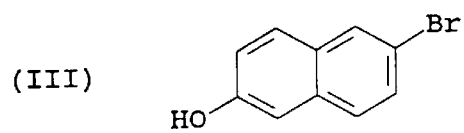
Figure 1A:
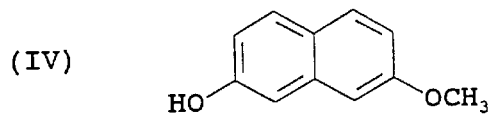
Figure 1A:
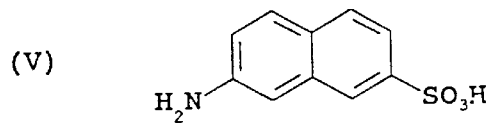
Figure 1A:
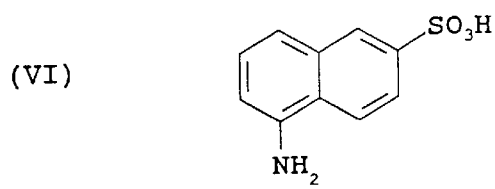
Figure 1A:
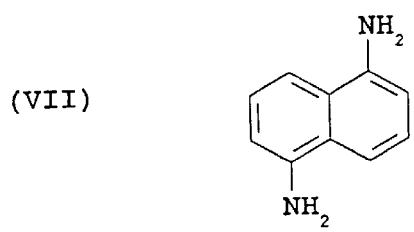
Figure 1A:
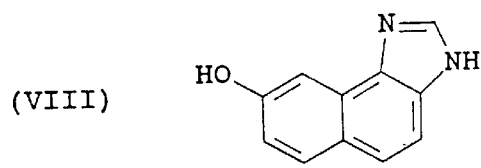
Figure 1B:
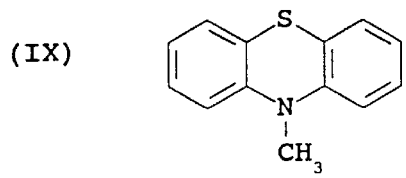
Figure 1B:
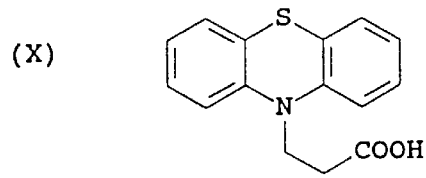
Figure 1B:
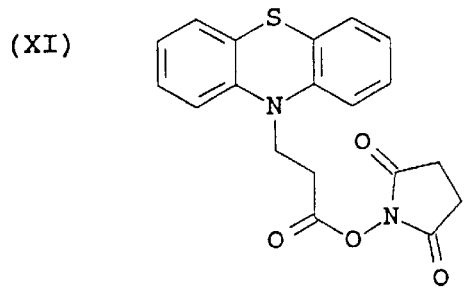
Figure 1B:
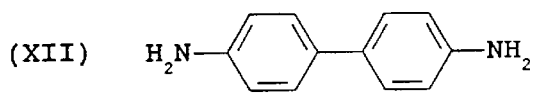
Figure 1B:
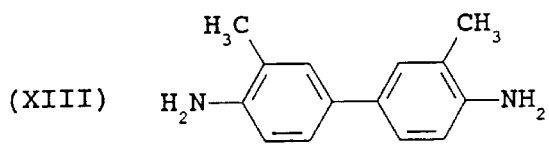
Figure 1B:
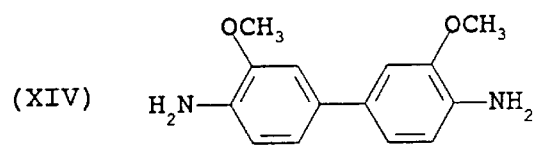
Figure 1B:
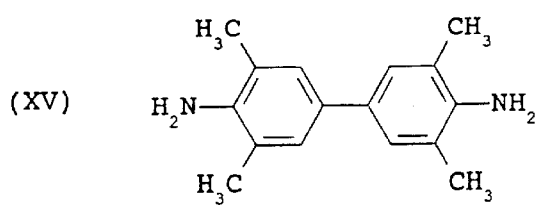
Figure 1B:
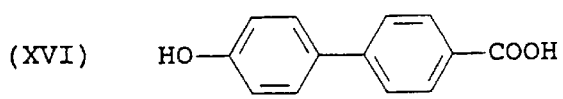
Figure 1C:
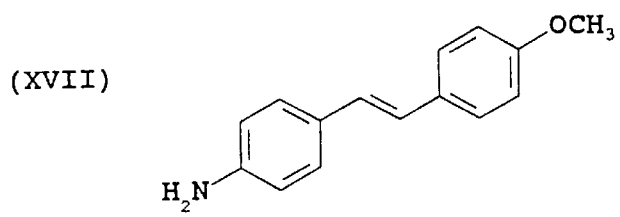
Figure 1C:
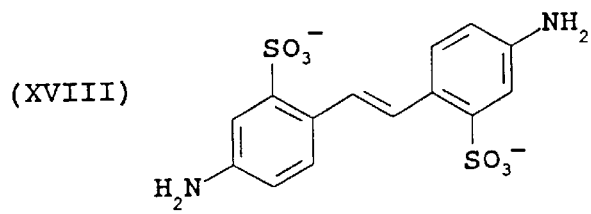
Figure 1C:
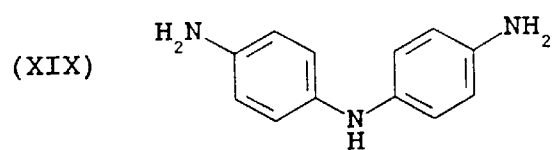
Figure 1C:
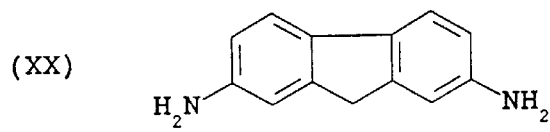
Figure 1C:
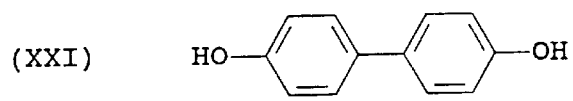
Figure 1C:
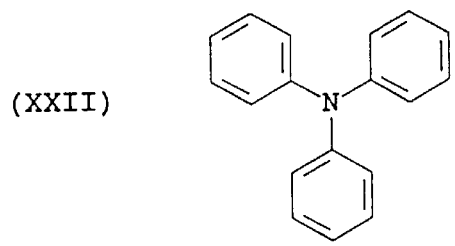
Figure 1D:
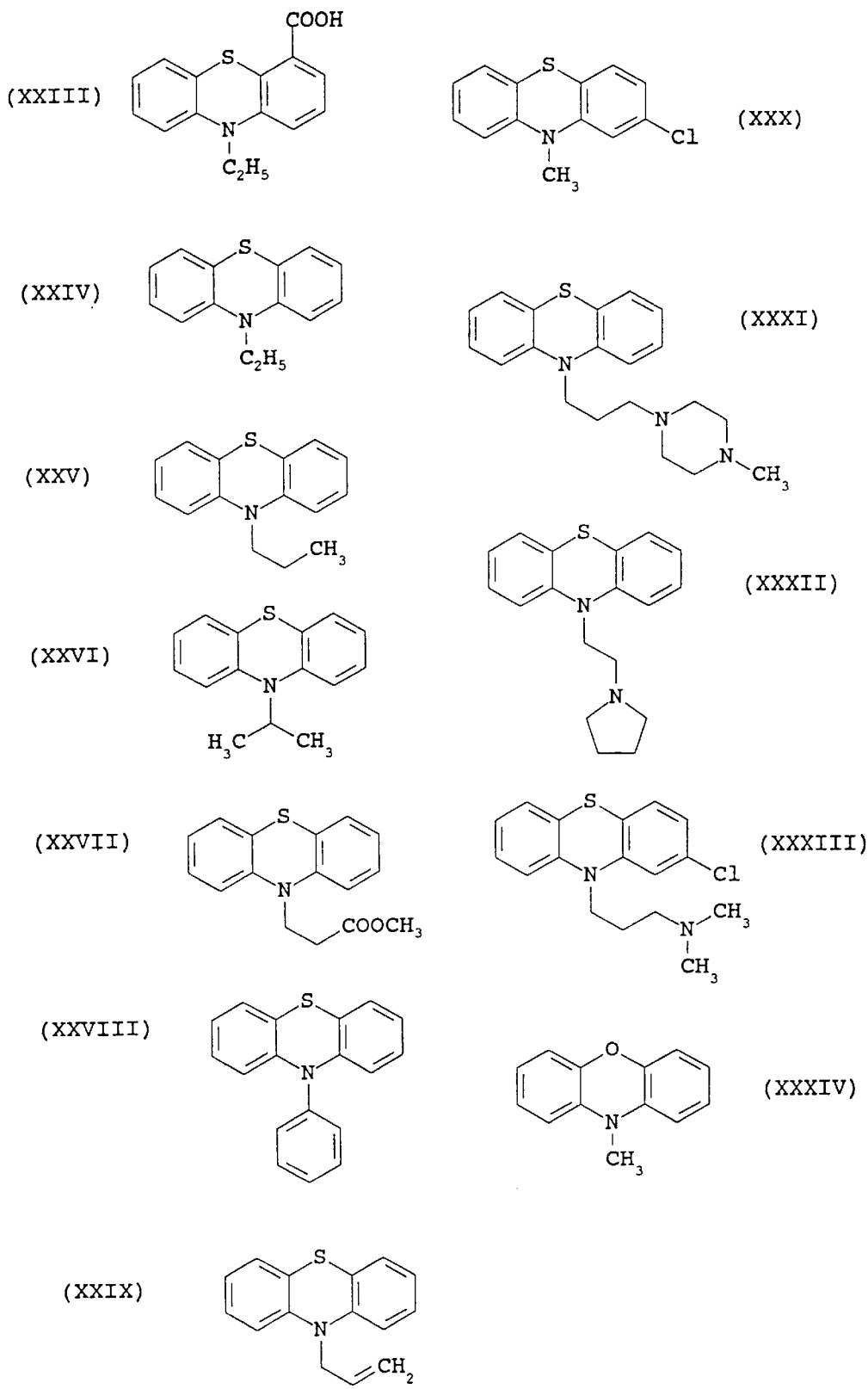
Figure 1E:
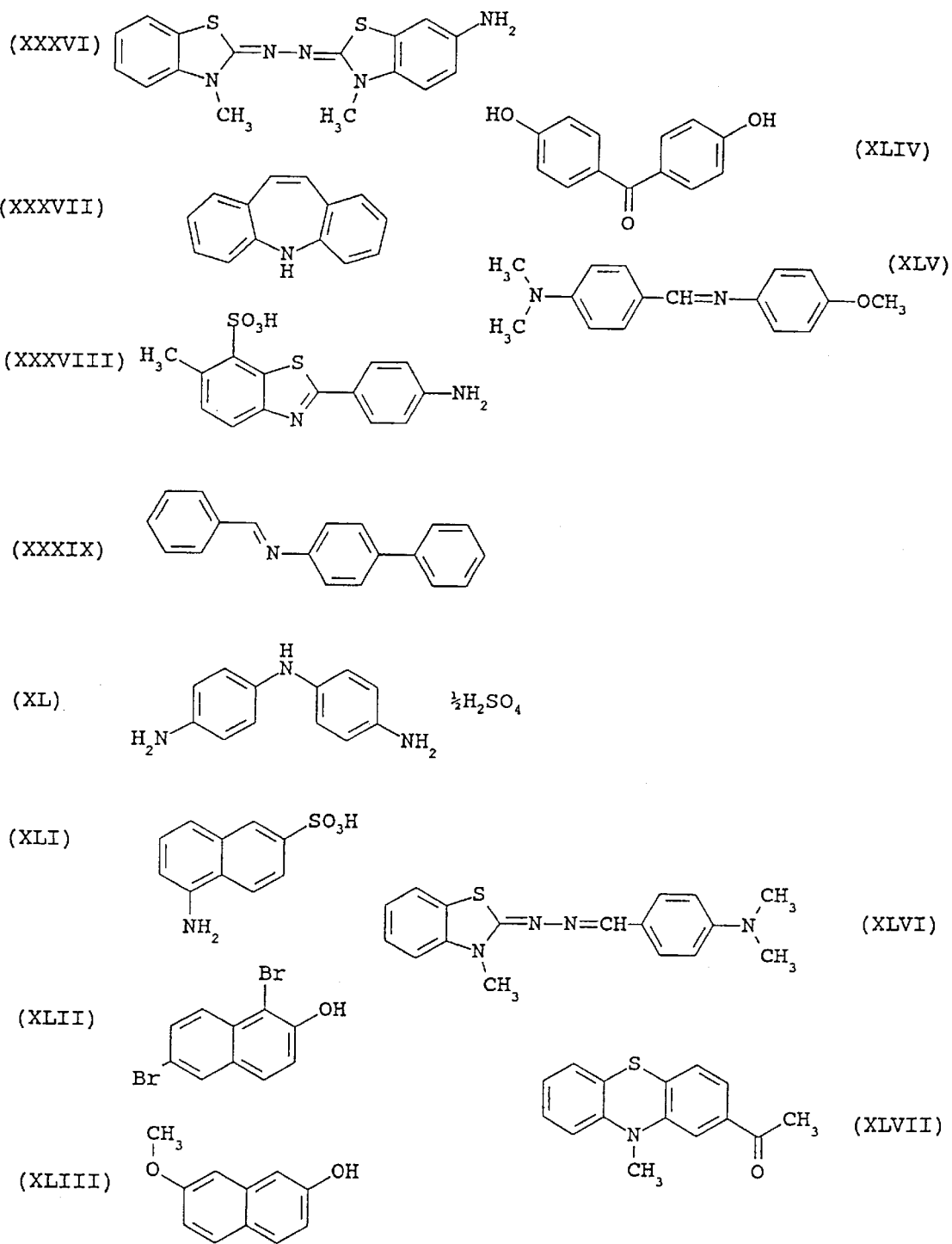

Determination of peroxidase activity: 1 peroxidase unit (PODU) is the amount of enzyme that catalyzes the conversion of 1 μmol hydrogen peroxide per minute at the following analytical conditions: 0.88 mM hydrogen peroxide, 1.67 mM 2,2'-azinobis (3-ethylbenzothiazoline-6-sulfonate), 0.1 M phosphate buffer, pH 7.0, incubated at 30° C., photometrically followed at 418 nm.

DETAILED DISCLOSURE OF THE INVENTION

The Enhancing Agent

The present invention relates to the use of chemical compounds for enhancing the activity of peroxidase enzymes or peroxidase acting compounds. Accordingly, the invention provides an agent capable of enhancing the effect of a peroxidase enzyme or a peroxidase acting compound, in the following termed enhancing agent.

Contrary to the enhancers known and previously described, the enhancing agents of this invention are capable of acting at alkaline conditions, i.e. at pH above 8. This feature allows the enhancers of the invention to be implemented into various industrial processes.

The enhancing agent of the invention is an organic chemical compound consisting of at least two aromatic rings, of which aromatic rings at least one ring is substituted with one or more nitrogen, oxygen, and/or sulfur atoms, and which aromatic rings may furthermore be fused rings.

In a more preferred embodiment, the enhancing agent of the invention is an organic chemical compound of the general formula I:

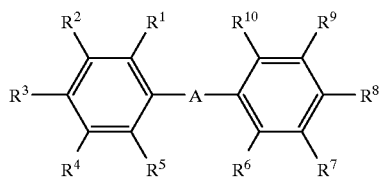

in which general formula A represents a single bond, or one of the following groups: $(-CR^{11}=CR^{15}-)_n$, $(-NR^{11}-)$, $(-CR^{11}=N-)_n$, $(-NR^{11}-CR^{12}=N-N=CR^{13}-NR^{15}-)$, $(-NR^{11}-CR^{12}=N-N=CR^{15}-)$, $(-NR^{11}-CR^{12}=N-)_n$, $(-CR^{12}=N-NR^{11}-)$, $(-NR^{11}-CR^{12}=CR^{13}-)$, $(-N=N-)$, in which groups n represents an integer of from 1 to 6; or A represents carbon, carbonyl, nitrogen, sulfur, oxygen, selenium, or phosphor, which carbon, phosphor and nitrogen may be unsubstituted or substituted with a substituent group $R^{11}$;

and in which general formula the substituent groups $R^1$–$R^{13}$ and $R^{15}$, which may be identical or different, independently represents any of the following radicals: hydrogen, halogen, hydroxy, formyl, carboxy and esters and salts hereof, carbamoyl, sulfo and esters and salts hereof, sulfamoyl, phospho, phosphono, phosphonooxy, sulfandiyl, nitro, amino, phenyl, $C_1$–$C_{14}$-alkyl, $C_1$–$C_5$-alkoxy, carbonyl-$C_1$–$C_5$-alkyl, aryl-$C_1$–$C_5$-alkyl; which carbamoyl, sulfamoyl, and amino groups may furthermore be unsubstituted or substituted once or twice with a substituent group $R^{14}$; and which phenyl may furthermore be unsubstituted or substituted with one or more substituent groups $R^{14}$; and which $C_1$–$C_{14}$-alkyl, $C_1$–$C_5$-alkoxy, carbonyl-$C_1$–$C_5$-alkyl, and aryl-$C_1$–$C_5$-alkyl groups may be saturated or unsaturated, branched or unbranched, and may furthermore be unsubstituted or substituted with one or more substituent groups $R^{14}$;

which substituent group $R^{14}$ represents any of the following radicals: halogen, hydroxy, formyl, carboxy and esters and salts hereof, carbamoyl, sulfo and esters and salts hereof, sulfamoyl, nitro, amino, phenyl, aminoalkyl, piperidino, piperazinyl, pyrrolidino, $C_1$–$C_5$-alkyl, $C_1$–$C_5$-alkoxy; which carbamoyl, sulfamoyl, and amino groups may furthermore be unsubstituted or substituted once or twice with hydroxy, $C_1$–$C_5$-alkyl, $C_1$–$C_5$-alkoxy; and which phenyl may furthermore be substituted with one or more of the following radicals: halogen, hydroxy, amino, formyl, carboxy and esters and salts hereof, carbamoyl, sulfo and esters and salts hereof, and sulfamoyl; and which $C_1$–$C_5$-alkyl, and $C_1$–$C_5$-alkoxy groups may furthermore be saturated or unsaturated, branched or unbranched, and may furthermore be substituted once or twice with any of the following radicals: halogen, hydroxy, amino, formyl, carboxy and esters and salts hereof, carbamoyl, sulfo and esters and salts hereof, and sulfamoyl;

or in which general formula $R^5$ and $R^6$ may together form a group —B—, in which B represents a single bond, the group (—CH=CH—)$_n$ or the group (—CH=N—)$_n$, in which groups n represents an integer of from 1 to 6; or B represents carbon, nitrogen, sulfur, oxygen, selenium, or tellurium, which carbon and nitrogen may be unsubstituted or substituted with a substituent group $R^{14}$ as defined above;

or in which general formula two of the substituent groups $R^1$–$R^{10}$ may together form a group —C—, in which C represents any of the following groups: (—CHR$^{11}$—N=N—), (—CH=CH—)$_n$, (—CH=N—)$_n$, in which groups n represents an integer of from 2 to 4, and in which groups $R^{11}$ is a substituent group as defined above;

or in which general formula $R^5$ and $R^{12}$, and/or $R^6$ and $R^{13}$, when n in the above formula being 1, may together form a group —D—, in which D represents the groups: (—CHR$^{11}$—), (—NR$^{11}$—), (—CR$^{11}$=CR$^{15}$—), (—CR$^{11}$=N—), (—N=CR$^{11}$—), (—O—), (>C=O) or (—S—), and in which groups $R^{11}$ and $R^{15}$ are substituent groups as defined above.

In particular embodiments, the enhancing agent is 2,2'-azino-bis(3-ethylbenzothiazoline-6-sulfonate), 6-amino-3-methyl-2-benzothiazolinone azine with 3-methyl-2-benzothiazolinone, 2-(p-aminophenyl)-6-methylbenzothiazole-7-sulfonic acid, N-(4-(dimethylamino)benzylidene)-p-anisidine, 3-methyl-2-benzothiazolinone(4-(dimethylamino)benzylidene)hydrazone.

In another preferred embodiment, the enhancing agent of the invention is an organic chemical compound of the general formula II:

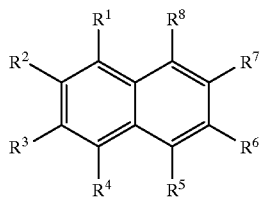

in which the substituent groups $R^1$–$R^8$, which may be identical or different, independently represents any of the following radicals: hydrogen, halogen, hydroxy, formyl, carboxy and esters and salts hereof, carbamoyl, sulfo and esters and salts hereof, sulfamoyl, nitro, amino, phenyl, $C_1$–$C_{14}$-alkyl, $C_1$–$C_5$-alkoxy, carbonyl-$C_1$–$C_5$-alkyl, aryl-$C_1$–$C_5$-alkyl; which carbamoyl, sulfamoyl, and amino groups may furthermore be unsubstituted or substituted once or twice with a substituent group $R^9$; and which phenyl may furthermore be unsubstituted or substituted with one or more substituent groups $R^9$; and which $C_1$–$C_{14}$-alkyl, $C_1$–$C_5$-alkoxy, carbonyl-$C_1$–$C_5$-alkyl, and aryl-$C_1$–$C_5$-alkyl groups may be saturated or unsaturated, branched or unbranched, and may furthermore be unsubstituted or substituted with one or more substituent groups $R^9$;

which substituent group $R^9$ represents any of the following radicals: halogen, hydroxy, formyl, carboxy and esters and salts hereof, carbamoyl, sulfo and esters and salts hereof, sulfamoyl, nitro, amino, phenyl, $C_1$–$C_5$-alkyl, $C_1$–$C_5$-alkoxy; which carbamoyl, sulfamoyl, and amino groups may furthermore be unsubstituted or substituted once or twice with hydroxy, $C_1$–$C_3$-alkyl, $C_1$–$C_3$-alkoxy; and which phenyl may furthermore be substituted with one or more of the following radicals: halogen, hydroxy, amino, formyl, carboxy and esters and salts hereof, carbamoyl, sulfo and esters and salts hereof, and sulfamoyl; and which $C_1$–$C_5$-alkyl, and $C_1$–$C_5$-alkoxy groups may furthermore be saturated or unsaturated, branched or unbranched, and may furthermore be substituted once or twice with any of the following radicals: halogen, hydroxy, amino, formyl, carboxy and esters and salts hereof, carbamoyl, sulfo and esters and salts hereof, and sulfamoyl;

or in which general formula two of the substituent groups $R^1$–$R^8$ may together form a group —B—, in which B represents any of the following groups: (—N=N—), (—CH=CH—)$_n$, (—CH=N—)$_n$, (—N=CR$^9$—NR$^{10}$—) or (—N=N—CR$^9$—), in which groups n represents an integer of from 1 to 3, $R^9$ is a substituent group as defined above and $R^{10}$ is defined as $R^9$.

In a more specific embodiment, the enhancing agent of the invention is an organic chemical compound of the following formula:

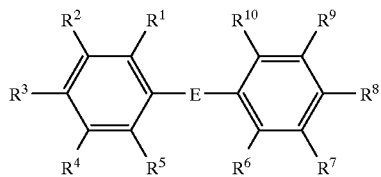

in which formula E represents a single bond, a carbonyl group or one of the following groups: (—CH=CH—)$_n$, (—CH=N—)$_n$ or (—NR$^{11}$—), in which n represents an integer from 1 to 2. The substituents groups $R^1$–$R^{11}$ may be identical or different, independently being one of the following radicals: hydrogen, halogen, hydroxy, formyl, carboxy and esters and salts hereof, carbamoyl, sulfo and esters and salts hereof, sulfamoyl, nitro, amino, phenyl, $C_1$–$C_{14}$-alkyl, $C_1$–$C_5$-alkoxy, carbonyl-$C_1$–$C_5$-alkyl, aryl-$C_1$–$C_5$-alkyl; which carbamoyl, sulfamoyl, and amino groups may furthermore be unsubstituted or substituted once or twice with a substituent group $R^{14}$; and which phenyl may furthermore be unsubstituted or substituted with one or more substituent groups $R^{14}$; and which $C_1$–$C_{14}$-alkyl, $C_1$–$C_5$-alkoxy, carbonyl-$C_1$–$C_5$-alkyl, and aryl-$C_1$–$C_5$-alkyl groups may be saturated or unsaturated, branched or unbranched, and may furthermore be unsubstituted or substituted with one or more substituent groups $R^{14}$;

which substituent group $R^{14}$ represents any of the following radicals: halogen, hydroxy, formyl, carboxy and esters and salts hereof, carbamoyl, sulfo and esters and salts hereof, sulfamoyl, nitro, amino, phenyl, $C_1$–$C_5$-alkyl, $C_1$–$C_5$-alkoxy; which carbamoyl, sulfamoyl, and amino groups may furthermore be unsubstituted or substituted once or twice with hydroxy, $C_1$–$C_3$-alkyl, $C_1$–$C_3$-alkoxy; and which phenyl may furthermore be substituted with one or more of the following radicals: halogen, hydroxy, amino, formyl, carboxy and esters and salts hereof, carbamoyl, sulfo and esters and salts hereof, and sulfamoyl; and which $C_1$–$C_5$-alkyl, and $C_1$–$C_5$-alkoxy groups may furthermore be saturated or unsaturated, branched or unbranched, and may furthermore be substituted once or twice with any of the following radicals: halogen, hydroxy, amino, formyl, carboxy and esters and salts hereof, carbamoyl, sulfo and esters and salts hereof, and sulfamoyl;

or in which specific formula two of the substituent groups $R^5$ and $R^6$ may together form a group —B—, in which B represents the groups: (—CH=N—)$_n$, (—CH=CH—) or (—CHR$^{14}$—) in which groups n represents an integer of from 1 to 2 and $R^{14}$ is a substituent group as defined above.

In particular embodiments, the enhancing agent is 4-amino-4'-methoxystilbene, 4,4'-diaminostilbene-2,2'-disulfonic acid, iminostilbene, 4,4'-dihydroxybenzophenone, N-benzylidene-4-biphenylamine, 4,4'-diaminodiphenylamine, 4,4'-diaminodiphenylaminesulfate, 2,7-diaminofluorene, triphenylamine.

In another specific embodiment, the enhancing agent may be described by the following formula:

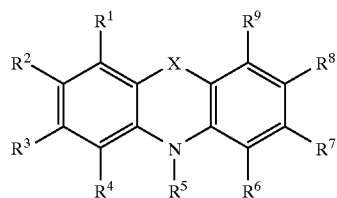

in which formula X represents one of the following groups: (—O—), (—S—), (—NR$^{15}$—), (—CHR$^{15}$—), (>C=O), (—CH=CH—), (—CH=N—) and the substituent groups $R^1$–$R^9$ and $R^{15}$, which may be identical or different, independently represents any of the following radicals: hydrogen, halogen, hydroxy, formyl, carboxy and esters and salts hereof, carbamoyl, sulfo and esters and salts hereof, sulfamoyl, nitro, amino, phenyl, $C_1$–$C_{14}$-alkyl, $C_1$–$C_5$-alkoxy, carbonyl-$C_1$–$C_5$-alkyl, aryl-$C_1$–$C_5$-alkyl; which carbamoyl, sulfamoyl, and amino groups may furthermore be unsubstituted or substituted once or twice with a substituent group $R^{10}$; and which phenyl may furthermore be unsubstituted or substituted with one or more substituent groups $R^{10}$; and which $C_1$–$C_{14}$-alkyl, $C_1$–$C_5$-alkoxy, carbonyl-$C_1$–$C_5$-alkyl, and aryl-$C_1$–$C_5$-alkyl groups may be saturated or unsaturated, branched or unbranched, and may furthermore be unsubstituted or substituted with one or more substituent groups $R^{10}$;

which substituent group $R^{10}$ represents any of the following radicals: halogen, hydroxy, formyl, carboxy and esters and salts hereof, carbamoyl, sulfo and esters and salts hereof, sulfamoyl, nitro, amino, phenyl, aminoalkyl, piperidino, piperazinyl, pyrrolidino, $C_1$–$C_5$-alkyl, $C_1$–$C_5$-alkoxy; which carbamoyl, sulfamoyl, and amino groups may furthermore be unsubstituted or substituted once or twice with hydroxy, $C_1$–$C_5$-alkyl, $C_1$–$C_5$-alkoxy; and which phenyl may furthermore be substituted with one or more of the following radicals: halogen, hydroxy, amino, formyl, carboxy and esters and salts hereof, carbamoyl, sulfo and esters and salts hereof, and sulfamoyl; and which $C_1$–$C_5$-alkyl, and $C_1$–$C_5$-alkoxy groups may furthermore be saturated or unsaturated, branched or unbranched, and may furthermore be substituted once or twice with any of the following radicals: halogen, hydroxy, amino, formyl, carboxy and esters and salts hereof, carbamoyl, sulfo and esters and salts hereof, and sulfamoyl;

or in which general formula two of the substituent groups $R^1$–$R^8$ may together form a group —B—, in which B represents any of the following the groups: (—CHR$^{10}$—N=N—), (—CH=CH—)$_n$, (—CH=N—)$_n$ or (—N=CR$^{10}$—NR$^{11}$—), in which groups n represents an integer of from 1 to 3, $R^{10}$ is a substituent group as defined above and $R^{11}$ is defined as $R^{10}$.

In particular embodiments, the enhancing agent is 10-methylphenothiazine, 10-phenothiazine-propionic acid, N-hydroxysuccinimide-10-phenothiazine-propionate or 10-ethyl-4-phenothiazine-carboxylic acid, 10-ethylphenothiazine, 10-propylphenothiazine, 10-isopropylphenothiazine, methyl-10-phenothiazinepropionate, 10-phenylphenothiazine,10-allylphenothiazine, 10-(3-(4-methyl-1-piperazinyl)propyl) phenothiazine, 10-(2-pyrrolidinoethyl)phenothiazine, chlorpromazine, 2-chloro-10-methylphenothiazine, 2-acetyl-10-methylphenothiazine, 4-carboxy-10-phenothiazine, 10-methylphenoxazine, 10-ethylphenoxazine, 10-phenoxazine-propionic acid or 4-carboxy-10-phenoxazine-propionic acid.

In another specific embodiment, enhancing agent is a biphenyl derivative of the following formula:

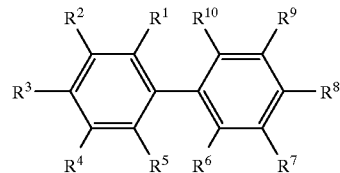

in which the substituent groups $R^1$–$R^{10}$, which may be identical or different, independently represents any of the following radicals: hydrogen, halogen, hydroxy, formyl, carboxy and esters and salts hereof, carbamoyl, sulfo and esters and salts hereof, sulfamoyl, nitro, amino, phenyl, $C_1$–$C_{14}$-alkyl, $C_1$–$C_5$-alkoxy, carbonyl-$C_1$–$C_5$-alkyl, aryl-$C_1$–$C_5$-alkyl; which carbamoyl, sulfamoyl, and amino groups may furthermore be unsubstituted or substituted once or twice with a substituent group $R^{11}$; and which phenyl may furthermore be unsubstituted or substituted with one or more substituent groups $R^{11}$; and which $C_1$–$C_{14}$-alkyl, $C_1$–$C_5$-alkoxy, carbonyl-$C_1$–$C_5$-alkyl, and aryl-$C_1$–$C_5$-alkyl groups may be saturated or unsaturated, branched or unbranched, and may furthermore be unsubstituted or substituted with one or more substituent groups $R^{11}$;

which substituent group $R^{11}$ represents any of the following radicals: halogen, hydroxy, formyl, carboxy and esters and salts hereof, carbamoyl, sulfo and esters and salts hereof, sulfamoyl, nitro, amino, phenyl, $C_1$–$C_5$-alkyl, $C_1$–$C_5$-alkoxy; which carbamoyl, sulfamoyl, and amino groups may furthermore be unsubstituted or substituted once or twice with hydroxy, $C_1$–$C_3$-alkyl, $C_1$–$C_3$-alkoxy; and which phenyl may furthermore be substituted with one or more of the following radicals: halogen, hydroxy, amino, formyl, carboxy and esters and salts hereof, carbamoyl, sulfo and esters and salts hereof, and sulfamoyl; and which $C_1$–$C_5$-alkyl, and $C_1$–$C_5$-alkoxy groups may furthermore be saturated or unsaturated, branched or unbranched, and may furthermore be substituted once or twice with any of the following radicals: halogen, hydroxy, amino, formyl, carboxy and esters and salts hereof, carbamoyl, sulfo and esters and salts hereof, and sulfamoyl.

In particular embodiments, the enhancing agent is benzidine, 3,3'-dimethylbenzidine, 3,3'-dimethoxybenzidine, 3,3',5,5'-tetramethylbenzidine, 4'-hydroxy-4-biphenylcarboxylic acid, or 4,4'-dihydroxybiphenylene.

In another specific embodiment, the enhancing agent is a naphthalene derivative of the following formula:

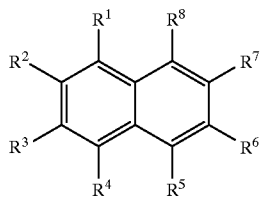

in which the substituent groups $R^1$–$R^8$, which may be identical or different, independently represents any of the following radicals: hydrogen, halogen, hydroxy, formyl, carboxy and esters and salts hereof, carbamoyl, sulfo and esters and salts hereof, sulfamoyl, nitro, amino, phenyl, $C_1$–$C_{14}$-alkyl, $C_1$–$C_5$-alkoxy, carbonyl-$C_1$–$C_5$-alkyl, aryl-$C_1$–$C_5$-alkyl; which carbamoyl, sulfamoyl, and amino groups may furthermore be unsubstituted or substituted once or twice with a substituent group $R^9$; and which phenyl may furthermore be unsubstituted or substituted with one or more substituent groups $R^9$; and which $C_1$–$C_{14}$-alkyl, $C_1$–$C_5$-alkoxy, carbonyl-$C_1$–$C_5$-alkyl, and aryl-$C_1$–$C_5$-alkyl groups may be saturated or unsaturated, branched or unbranched, and may furthermore be unsubstituted or substituted with one or more substituent groups $R^9$;

which substituent group $R^9$ represents any of the following radicals: halogen, hydroxy, formyl, carboxy and esters and salts hereof, carbamoyl, sulfo and esters and salts hereof, sulfamoyl, nitro, amino, phenyl, $C_1$–$C_5$-alkyl, $C_1$–$C_5$-alkoxy; which carbamoyl, sulfamoyl, and amino groups may furthermore be unsubstituted or substituted once or twice with hydroxy, $C_1$–$C_3$-alkyl, $C_1$–$C_3$-alkoxy; and which phenyl may furthermore be substituted with one or more of the following radicals: halogen, hydroxy, amino, formyl, carboxy and esters and salts hereof, carbamoyl, sulfo and esters and salts hereof, and sulfamoyl; and which $C_1$–$C_5$-alkyl, and $C_1$–$C_5$-alkoxy groups may furthermore be saturated or unsaturated, branched or unbranched, and may furthermore be substituted once or twice with any of the following radicals: halogen, hydroxy, amino, formyl, carboxy and esters and salts hereof, carbamoyl, sulfo and esters and salts hereof, and sulfamoyl;

or in which general formula two of the substituent groups $R^1$–$R^8$ may together form a group —B—, in which B represents any of the following groups: (—N=N—), (—CH=CH—)$_n$, (—CH=N—)$_n$, (—N=CR$^9$—NR$^{10}$—) or (—N=N—CR$^9$—), in which groups n represents an integer of from 1 to 3, $R^9$ is a substituent group as defined above and $R^{10}$ is defined as $R^9$.

In particular embodiments, the enhancing agent is 6-hydroxy-2-naphtoic acid, 6-bromo-2-naphtol, 7-methoxy-2-naphtol, 7-amino-2-naphthalene sulfonic acid, 5-amino-2-naphthalene sulfonic acid, 1,5-diaminonaphthalene, 7-hydroxy-1,2-naphthimidazole, 5-amino-2-naphthalenesulfonic acid, 1,6-dibromo-2-naphtol or 7-methoxy-2-naphtol.

The enhancing agent of the invention may be in free form or in the form of an addition salt.

Methods of Oxidizing a Substrate

In another aspect, the invention provides a method of oxidizing a substrate with a source of hydrogen peroxide in the presence of a peroxidase enzyme or a peroxidase acting compound, in the presence of an enhancing agent of the invention.

The enhancing agent of the invention may be present in free form or in the form of an addition salt.

The enhancing agent of the invention may be present in concentrations of from 0.01 to 500 $\mu$M, more preferred 0.1 to 250 $\mu$M, most preferred 1 to 100 $\mu$M.

The source of hydrogen peroxide may be hydrogen peroxide or a hydrogen peroxide precursor for in situ production of hydrogen peroxide, e.g. percarbonate or perborate, or a hydrogen peroxide generating enzyme system, e.g. an oxidase and a substrate for the oxidase or an amino acid oxidase and a suitable amino acid, or a peroxycarboxylic acid or a salt thereof. Hydrogen peroxide may be added at the beginning or during the process, e.g. in an amount of 0.001–5 mM, particularly 0.01–1 mM.

Peroxidases and Peroxidase Acting Compounds

The enzyme employed in the method of the invention may be any peroxidase enzyme comprised by the enzyme classification EC 1.11.1.7, or any fragment derived therefrom, exhibiting peroxidase activity, or synthetic or semisynthetic derivatives thereof (e.g. porphyrin ring systems or microperoxidases, cf. e.g. U.S. Pat. No. 4,077,768, EP Patent Application 537,381, International Patent Applications WO 91/05858 and WO 92/16634). Such enzymes are known from microbial, plant and animal origins.

Preferably, the peroxidase employed in the method of the invention is producible by plants (e.g. horseradish or soy bean peroxidase) or microorganisms such as fungi or bacteria. Some preferred fungi include strains belonging to the subdivision Deuteromycotina, class Hyphomycetes, e.g. Fusarium, Humicola, Tricoderma, Myrothecium, Verticillum, Arthromyces, Caldariomyces, Ulocladium, Embellisia, Cladosporium or Dreschlera, in particular *Fusarium oxysporum* (DSM 2672), *Humicola insolens, Trichoderma resii, Myrothecium verrucana* (IFO 6113), *Verticillum alboatrum, Verticillum dahlie, Arthromyces ramosus* (FERM P-7754), *Caldariomyces fumago, Ulocladium chartarum, Embellisia alli* or *Dreschlera halodes.*

Other preferred fungi include strains belonging to the subdivision Basidiomycotina, class Basidiomycetes, e.g. Coprinus, Phanerochaete, Coriolus or Trametes, in particular *Coprinus cinereus* f. *microsporus* (IFO 8371), *Coprinus macrorhizus, Phanerochaete chrysosporium* (e.g. NA-12) or Trametes (previously called Polyporus), e.g. *T. versicolor* (e.g. PR4 28-A).

Further preferred fungi include strains belonging to the subdivision Zygomycotina, class Mycoraceae, e.g. Rhizopus or Mucor, in particular *Mucor hiemalis.*

Some preferred bacteria include strains of the order Actinomycetales, e.g. *Streptomyces spheroides* (ATTC 23965), *Streptomyces thermoviolaceus* (IFO 12382) or *Streptoverticillum verticillium* ssp. *verticillium.*

Other preferred bacteria include *Bacillus pumilus* (ATCC 12905), *Bacillus stearothermophilus, Rhodobacter sphaeroides, Rhodomonas palustri, Streptococcus lactis, Pseudomonas purrocinia* (ATCC 15958) or *Pseudomonas fluorescens* (NRRL B-11).

Further preferred bacteria include strains belonging to Myxococcus, e.g. *M. virescens.*

Other potential sources of useful particular peroxidases are listed in Saunders B C, op. cit., pp. 41–43.

The peroxidase may furthermore be one which is producible by a method comprising cultivating a host cell transformed with a recombinant DNA vector which carries a DNA sequence encoding said peroxidase as well as DNA sequences encoding functions permitting the expression of the DNA sequence encoding the peroxidase, in a culture medium under conditions permitting the expression of the peroxidase and recovering the peroxidase from the culture.

Particularly, a recombinantly produced peroxidase is a peroxidase derived from a Coprinus sp., in particular *C. macrorhizus* or *C. cinereus* according to WO 92/16634.

In the context of this invention, peroxidase acting compounds comprise peroxidase active fragments derived from cytochromes, hemoglobin or peroxidase enzymes, and synthetic or semisynthetic derivatives thereof, e.g. iron porphins, iron porphyrins, and iron phthalocyanine and derivatives thereof.

INDUSTRIAL APPLICATIONS

Due to their excellent performance at alkaline conditions, the enhancing agents of the invention, and hence the method for oxidizing a substrate with a peroxidase enzyme or a peroxidase acting compound in the presence of a source of hydrogen peroxide and in the presence of an enhancing of the invention, find various industrial applications In a preferred embodiment, the method of the invention finds application for bleaching of dye in solutions.

In another embodiment, the method of the invention finds application for dye transfer inhibition, e.g. for treatment of dyed textiles (cf. e.g. WO 92/18687) or during laundering (cf. e.g. WO 91/05839).

Accordingly, in a specific embodiment, the invention provides a method for inhibiting the transfer of a textile dye from a dyed fabric to another fabric when said fabrics are washed together in a wash liquor, the method comprising treatment of the wash liquor with a peroxidase enzyme or a peroxidase acting compound in the presence of a source of hydrogen peroxide, and in the presence of an enhancing agent of the invention. The textile dye may be a synthetic dye such as an azo dye, or a natural or nature-identical dye.

In a third embodiment, the method of the invention finds application in bleaching of pulp for paper production. The use of a peroxidase together with hydrogen peroxide or a hydrogen peroxide precursor in bleaching of paper pulp has been described in e.g. SE 88/0673 and U.S. Pat. No. 4,690,895.

Accordingly, the invention provides a method for bleaching of lignin-containing material, in particular bleaching of pulp for paper production, which method comprises treatment of the lignin or lignin containing material with a peroxidase enzyme or a peroxidase acting compound in the presence of a source of hydrogen peroxide and in the presence of an enhancing agent of the invention.

In a fourth embodiment, the method of the invention finds application for lignin modification, e.g. in particle board production. Binders for producing wood composites such as fibre boards and particle boards can be made from peroxidase treated lignin (cf. U.S. Pat. No. 4,432,921).

Accordingly, the invention provides a method for enzymatic polymerization and/or modification of lignin or lignin containing material, which method comprises treatment of the lignin or lignin containing material with a peroxidase or a peroxidase acting compound in the presence of a source of hydrogen peroxide, and in the presence of an enhancing agent of the invention.

In a fifth embodiment, the method of the invention finds application in treatment of waste water e.g. waste water from the chemical or pharmaceutical industry, from dye manufacturing, from dye-works, from the textile industry, or from pulp production (cf. e.g. U.S. Pat. No. 4,623,465, or JP-A-2-31887).

In a more specific aspect, the invention provides a method for treatment of waste water from dye manufacturing, from dye-works, from textile industry, or from pulp manufacturing, the method comprising treatment of the waste water with a peroxidase or a peroxidase acting compound in the presence of a source of hydrogen peroxide and in the presence of an enhancing agent of the invention.

Detergent Compositions

Due to their excellent performance at alkaline conditions the enhancing agents of the invention are particularly well suited for implementation into detergent compositions, intended for performance in the range of pH 7–13, particularly the range of pH 8–12, preferably the range of pH 8–11.

According to the invention, the enhancing agent may be added as a component of a detergent composition. As such, it may be included in the detergent composition in the form of a detergent additive. The detergent composition as well as the detergent additive may additionally comprise one or more other enzymes conventionally used in detergents, such as proteases, lipases, amylases, oxidases, and cellulases.

In a specific aspect, the invention provides a detergent additive. The enzymes may be included in a detergent composition by adding separate additives containing one or more enzymes, or by adding a combined additive comprising all of these enzymes. A detergent additive of the invention, i.e. a separated additive or a combined additive, can be formulated e.g. as granulates, liquids, slurries, etc. Preferred detergent additive formulations are granulates, in particular non-dusting granulates, liquids, in particular stabilized liquids, slurries, or protected enzymes.

Dust free granulates may be produced, e.g. as disclosed in U.S. Pat. No. 4,106,991 and U.S. Pat. No. 4,661,452, and may optionally be coated by methods known in the art. The detergent enzymes may be mixed before or after granulation.

Liquid enzyme preparations may, for instance, be stabilized using conventional stabilizing agents for the enzymes, as described below.

Protected enzymes may be prepared according to the method disclosed in EP 238,216 A.

In another specific aspect, the invention provides a detergent composition capable of inhibiting the transfer of textile dyes from dyed fabrics to other fabrics when said fabrics are washed together in a wash liquor, the detergent composition comprising an enzyme or compound exhibiting peroxidase activity, a source of hydrogen peroxide and an enhancing agent of the invention.

The enhancing agent of the invention may be included in the detergent composition as a part of a peroxidase system, comprising one or more peroxidase enzymes or peroxidase acting compounds, a source of hydrogen peroxide, and the enhancing agent of the invention.

The detergent composition of the invention may be in any convenient form, e.g. as powder, granules or liquid. A liquid detergent may be aqueous, typically containing up to 70% water and 0–20% organic solvent.

The detergent composition comprises one or more surfactants each of which may be anionic, non-ionic, cationic or amphoteric. The detergent will usually contain 5–30% of anionic surfactant such as linear alkylbenzenesulfonate (LAS), alpha-olefinsulfonate (AOS), alkyl sulfate (AS), alcohol ethoxysulfate (AES) or soap. It may also contain 3–20% of non-ionic surfactant such as nonylphenol ethoxylate or alcohol ethoxylate.

The detergent composition may additionally comprise one or more other enzymes, such as an amylase, lipase, cellulase or protease.

The detergent may contain 1–40% of a detergent builder such as zeolite, phosphate, phosphonate, citrate, nitrilotriacetic acid (NTA), ethylenediaminetetraacetic acid (EDTA) or diethylenetriaminepentaacetic acid (DTPA), alkenylsuccinic anhydride, or silicate, or it may be unbuilt (i.e. essentially free of a detergent builder). It may also contain other conventional detergent ingredients, e.g. fabric conditioners, foam boosters, anti-corrosion agents, soil-suspending agents, sequestering agents, anti-soil redeposition agents, stabilizing agents for the enzyme(s), foam depressors, dyes, bactericides, optical brighteners or perfumes.

The pH (measured in aqueous detergent solution) will usually be neutral or alkaline, e.g. 7–11.

Particular forms of detergent composition within the scope of the invention include:

a) A detergent composition formulated as a detergent powder containing phosphate builder, anionic surfactant, nonionic surfactant, silicate, alkali to adjust to desired pH in use, and neutral inorganic salt.

b) A detergent composition formulated as a detergent powder containing zeolite builder, anionic surfactant, nonionic surfactant, acrylic or equivalent polymer, silicate, alkali to adjust to desired pH in use, and neutral inorganic salt.

c) A detergent composition formulated as an aqueous detergent liquid comprising anionic surfactant, nonionic surfactant, organic acid, alkali, with a pH in use adjusted to a value between 7 and 11.

d) A detergent composition formulated as a nonaqueous detergent liquid comprising a liquid nonionic surfactant consisting essentially of linear alkoxylated primary alcohol, phosphate builder, alkali, with a pH in use adjusted to a value between about 7 and 11.

e) A compact detergent composition formulated as a detergent powder in the form of a granulate having a bulk density of at least 600 g/l, containing anionic surfactant and nonionic surfactant, phosphate builder, silicate, and little or substantially no neutral inorganic salt.

f) A compact detergent composition formulated as a detergent powder in the form of a granulate having a bulk density of at least 600 g/l, containing anionic surfactant and nonionic surfactant, zeolite builder, silicate, and little or substantially no neutral inorganic salt.

g) A detergent composition formulated as a detergent powder containing anionic surfactant, nonionic surfactant, acrylic polymer, fatty acid soap, carbonate, sulfate, clay particles, and silicate.

h) A liquid compact detergent comprising 5–65% by weight of surfactant, 0–50% by weight of builder and 0–30% by weight of electrolyte.

i) A compact granular detergent comprising linear alkylbenzenesulfonate, tallow alkyl sulfate, $C_{14-15}$ alkyl sulfate, $C_{14-15}$ alcohol 7 times ethoxylated, tallow alcohol 11 times ethoxylated, dispersant, silicone fluid, trisodium citrate, citric acid, zeolite, maleic acid/acrylic acid copolymer, diethylenetriaminepentakis (methylenephosphonic acid), cellulase, protease, lipase, amylase, sodium silicate, sodium sulfate, PVP, perborate and bleach activator.

j) A granular detergent comprising sodium linear $C_{11-12}$ alkylbenzenesulfonate, sodium sulfate, zeolite A, sodium nitrilotriacetate, cellulase, PVP, tetraacetylethylenediamine, boric acid and perborate.

k) A liquid detergent comprising $C_{12-14}$ alkenylsuccinic acid, citric acid, sodium $C_{12-15}$ alkyl sulfate, sodium sulfate of $C_{12-15}$ alcohol 2 times ethoxylated, $C_{12-15}$ alcohol 7 times ethoxylated, $C_{12-15}$ alcohol 5 times ethoxylated, diethylenetriaminepentakis(methylenephosphonic acid), oleic acid, ethanol, propanediol, protease, cellulase, PVP, suds supressor, sodium hydroxide, perborate and bleach activator.

The following examples further illustrate the present invention, and they are not intended to be in any way limiting to the scope of the invention as claimed.

EXAMPLE 1

Bleaching of Methyl Orange

*Coprinus cinereus* peroxidase (CiP) was obtained according to WO 92/16634, and purified to a single band on SDS-PAGE by the following method:

The crude peroxidase preparation was precipitated with 25% w/w anmoniumsulfate, and after centrifugation the precipitate was dissolved in 10 mM phosfate pH 7 (buffer A) and dialysed against the same buffer. The sample was applied onto a HighLoad Q-Sepharose column (Pharmacia, Sweden) equilibrated with buffer A, washed with buffer and eluted with a linear gradient of NaCl up to 0.5 M in the same buffer.

The main fraction containing peroxidase activity was collected, concentrated by ultrafiltration (with a membrane cut-off of 10 kD) and dialysed against buffer A.

The concentration of CiP was determined by $A_{404}$ using a molar absorption of 109 $mM^{-1}$ $cm^{-1}$.

Figure 2:
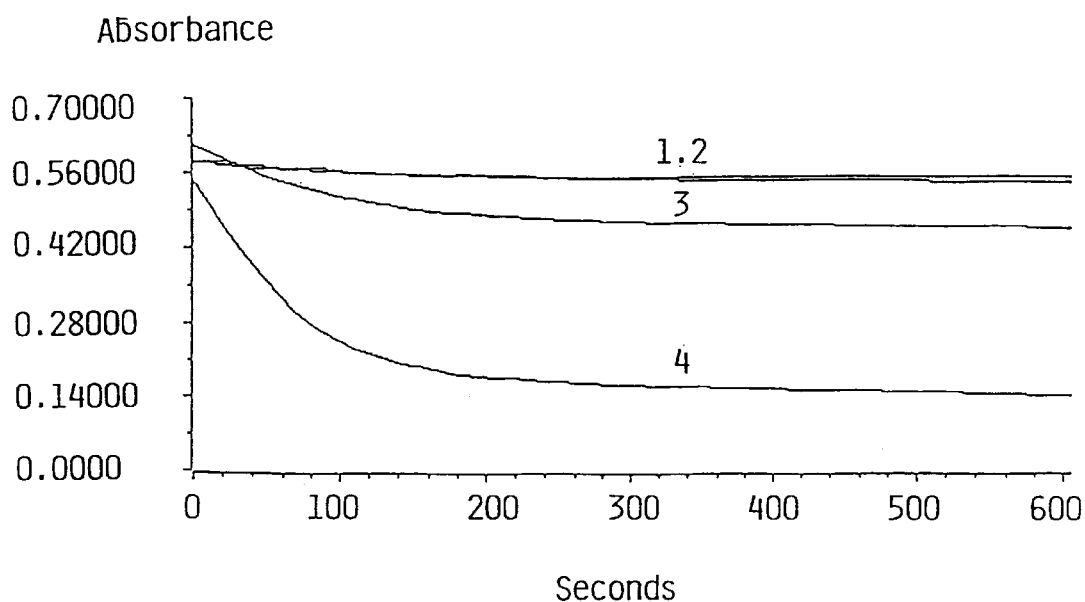
FIG. 2 shows a comparison of an enhancing agent of the invention (ABTS) and pHBS, applied to bleaching of Methyl Orange by a *Coprinus cinereus* peroxidase (1: pHBS, 20 μM $H_2O_2$; 2: pHBS, 200 μM $H_2O_2$; 3: ABTS, 20 μM $H_2O_2$; 4: ABTS, 200 μM $H_2O_2$)

Accelerated bleaching of Methyl orange (Merck) catalysed by CiP and hydrogen peroxide in the presence of 2,2'-azino-bis(3-ethylbenzothiazoline-6-sulfonate) (ABTS, supplied by Boehringer Mannheim) or para-hydroxybenzene sulfonate (pHBS, supplied by Sigma) is shown in FIG. 2. The following conditions were used:

10 nM CiP
25 $\mu$M Methyl Orange
50 $\mu$M ABTS or para-hydroxybenzene sulfonate
20 or 200 $\mu$M hydrogen peroxide
50 mM Britton & Robinson buffer*, pH 8.8
30° C. thermostat

*$H_3PO_4$, $CH_3CO_2H$, $H_3BO_3$, all three components at a concentration of 50 mM Reagents were mixed in a 1 cm cuvette, and the bleaching was started by addition of hydrogen peroxide. The bleaching was detected spectrophotometrically at 465 nm, which is the absorption peak of this dye. Bleaching was followed with respect to time over a span of 10 min.

EXAMPLE 2

Bleaching of Methyl Orange

Figure 3:
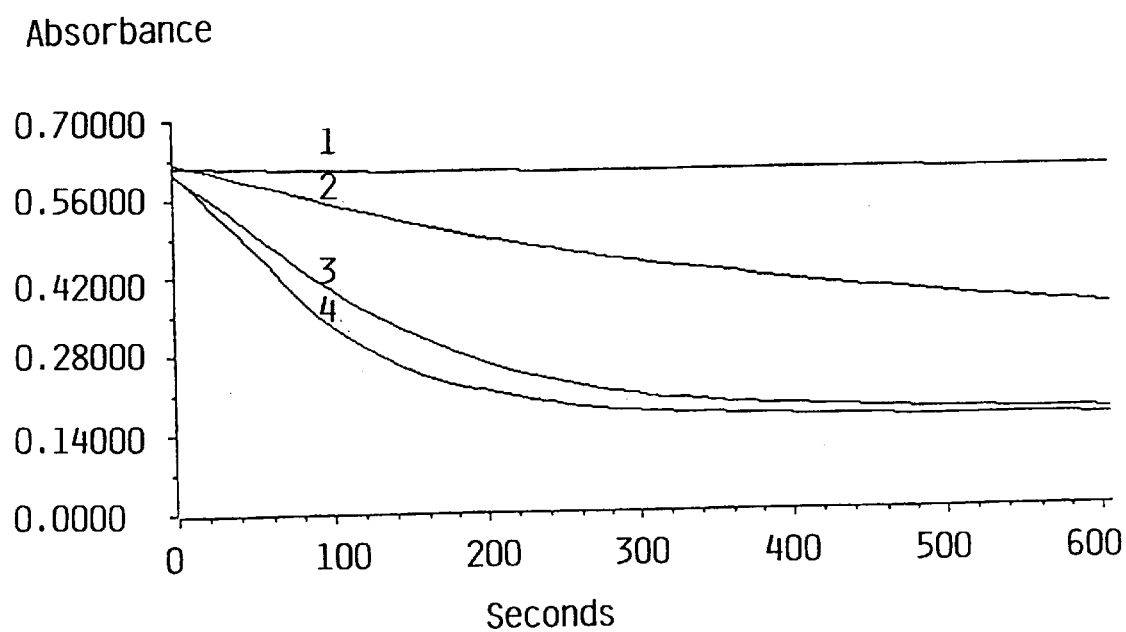
FIG. 3 shows accelerated bleaching of Methyl Orange by a *Coprinus cinereus* peroxidase in the presence of varying concentrations of an enhancing agent of the invention (ABTS) (1: 0 μM ABTS; 2: 1 μM ABTS; 3: 5 μM ABTS; and 4: 10 μM ABTS)

Accelerated bleaching of Methyl Orange (Merck) catalysed by a *Coprinus cinereus* peroxidase (CiP), obtained according to Example 1, and hydrogen peroxide in the presence of varying concentrations of 2,2'-azino-bis(3-ethylbenzothiazoline-6-sulfonate) (ABTS, supplied by Boehringer Mannheim) is shown in FIG. 3. The following conditions were used:

10 nM CiP
25 µM Methyl Orange
0, 1, 5 or 10 µM ABTS
200 µM hydrogen peroxide
50 µM Britton & Robinson buffer, pH 8.8
30° C. thermostat Mixture, start and detection of the bleaching are as described in Example 1.

EXAMPLE 3

Bleaching of Direct Blue 1

The initial bleaching of Direct Blue 1 (DB1) by a *Coprinus cinereus* peroxidase (CiP), obtained according to Example 1, using a selection of enhancers according to the invention was compared to the known enhancer, p-hydroxybenzene sulfonate, sodium salt (pHBS). Chemicals were obtained from Sigma-Aldrich, Janssen Chimica, Kodak, Tokyo Kasai Organic Chemicals, Daiichi Pure Chemicals Co. or Boehringer Mannheim, and some N-methylated derivatives of phenothiazine were made by methylation with methyliodide as described by Cornel Bodea and Ioan Silberg in "Recent Advances in the Chemistry of Phenothiazines" (Advances in heterocyclic chemistry, 1968, Vol. 9, pp. 321–460); B. Cardillo & G. Casnati in Tetrahedron, 1967, Vol. 23, p. 3771.

Due to low solubility some of the enhancers were dissolved in a small volume of ethanol before dilution in water.

The following conditions were used:

|  | Final concentration |
| --- | --- |
| 200 µl 50 mM Britton-Robinson buffer, pH 8.5 and 10.5, respectively, | 10 mM |
| 200 µl DB1 ~ 3.0 Abs. Units (610 nm) | 0.6 ($A_{610nm}$) |
| 200 µl 50 nM CiP in water | 10 nM |
| 200 µl 50 µM enhancer | 10 µM |
| 200 µl 100 µM $H_2O_2$ | 20 µM |

Reagents were mixed in a 1 cm thermostated cuvette at 30° C. and the bleaching was started by addition of hydrogen peroxide.

The bleaching was detected spectrophotometrically at 610 nm, which is the absorption peak of DB1. After 5 sec. bleaching was followed for 4 minutes, and the initial bleaching rates (reduction in milli-absorbance units per minute, $-\Delta mAbs/min$, determined from the initial slope of the absorbance curve after 5 sec.) as well as the total bleaching within 4 minutes ($100 \times (A_{610nm,start} - A_{610nm,4min})/A_{610nm,start}$ %) were determined.

$A_{610nm,start}$ was determined by replacement of hydrogen peroxide with water.

From the results presented in Table 1, below, it appears that the enhancers of the invention are superior to the known enhancer, pHBS, in initial bleaching of DB1, especially at high pH values.

Determination of the bleaching after 4 minutes is carried out to verify that a reasonable total bleaching can be obtained, and data are due to possible hydrogen peroxide deficiency not directly comparable.

TABLE 1

Bleaching of Direct Blue 1 at pH 8.5 and pH 10.5

| Enhancer | Initial DB1 bleaching ($-\Delta mAbs/min$) | | DB1 bleaching in 4 min. | |
| --- | --- | --- | --- | --- |
|  | pH 8.5 | pH 10.5 | pH 8.5 | pH 10.5 |
| ABTS | 1044 | 197 | 86% | 86% |
| 10-Phenothiazine-propionic acid | 1080 | 468 | 85% | 88% |
| 10-methyl-phenothiazine | 1176 | 480 | 85% | 87% |
| 4'-hydroxy-4-biphenyl-carboxylic acid | 588 | 68 | 57% | 39% |
| 3,3',5,5'-tetramethyl-benzidine | 960 | 266 | 63% | 49% |
| 4,4'-diaminostilbene-2,2'-disulfonic acid | 222 | 61 | 58% | 34% |
| 4-amino-4'-methoxy-stilbene | 132 | 72 | 46% | 26% |
| 1,5-diamino-naphthalene | 240 | 90 | 37% | 32% |
| 6-hydroxy-2-naphtoic acid | 486 | 52 | 46% | 32% |
| 10-ethyl-4-pheno-thiazinecarboxylic acid | 1146 | 864 | 85% | 89% |
| 10-ethylpheno-thiazine | 1098 | 624 | 83% | 84% |
| 10-propylpheno-thiazine | 1068 | 299 | 80% | 81% |
| 10-isopropylpheno-thiazine | 681 | 59 | 83% | 41% |
| methyl-10-pheno-thiazinepropionate | 840 | 99 | 86% | 67% |
| 10-phenylpheno-thiazine | 498 | 40 | 81% | 25% |
| 10-allylpheno-thiazine | 1170 | 183 | 86% | 80% |
| N-hydroxysuccin-imide-10-phenothi-azinepropionic acid | 1110 | 378 | 84% | 75% |
| 10-(3-(4-methyl-1-piperazinyl)propyl)phenothiazine | 1092 | 237 | 87% | 82% |
| 10-(2-pyrrolidino-ethyl)phenothia-zine | 444 | 160 | 86% | 80% |
| Chlorpromazine | 222 | 26 | 61% | 16% |
| 10-methylphenoxa-zine | 1464 | 792 | 79% | 81% |
| 6-amino-3-methyl-2-benzothiazolinone azine w. 3-methyl-2-benzothiazolinone | 96 | 42 | 54% | 29% |
| iminostilbene | 186 | 56 | 35% | 21% |
| 2-(p-aminophenyl)-6-methylbenzothia-zole-7-sulfonic acid | 114 | 26 | 25% | 11% |
| N-benzylidene-4-biphenylamine | 474 | 38 | 66% | 28% |
| 4,4'-diaminodiphe-nylaminesulfate | 378 | 28 | 59% | 8% |
| 5-amino-2-naphtha-lenesulfonic acid | 816 | 63 | 71% | 26% |
| 1,6-dibromo-2-naph-tol | 222 | 58 | 70% | 23% |
| 7-methoxy-2-naphtol | 480 | 84 | 46% | 29% |
| 4,4'-dihydroxyben-zophenone | 238 | 10 | 81% | 4% |
| N-(4-(dimethylami-no)benzylidene)-p-anisidine | 294 | 24 | 49% | 9% |

TABLE 1-continued

Bleaching of Direct Blue 1 at pH 8.5 and pH 10.5

| Enhancer | Initial DB1 bleaching (−ΔmAbs/min) | | DB1 bleaching in 4 min. | |
|---|---|---|---|---|
| | pH 8.5 | pH 10.5 | pH 8.5 | pH 10.5 |
| 3-methyl-2-benzo-thiazolinone(4-(di-methylamino)ben-zylidene)hydrazone | 378 | 26 | 66% | 8% |
| 2,7-diamino-fluorene,2HCl | 636 | 516 | 39% | 49% |
| 2-chloro-10-methylpheno-thiazine | 225 | 15 | 86% | 8% |
| 2-acetyl-10-methylpheno-thiazine | 270 | 25 | 88% | 18% |
| pHBS | 57 | ~0 | 42% | ~0% |
| No enhancer | 25 | ~0 | 18% | ~0% |

EXAMPLE 4

Bleaching of Direct Blue 1 with ABTS

The initial bleaching of Direct Blue 1 (DB1) by a *Coprinus cinereus* peroxidase (CiP), obtained according to Example 1, using ABTS as accelerator, was compared to the best of the hitherto known accelerators: 7-hydroxycoumarin (7HCm), vanillin (VAN), and p-hydroxybenzene sulfonate (pHBS). The following conditions were used:
1 nM CiP or 100 nM CiP (at pH 10.5)
0, 10, 25, 50, or 75 $\mu$M accelerator, respectively
50 mM Britton & Robinson buffer, pH 8.8 or 10.5, respectively
20 $\mu$M hydrogen peroxide Reagents were mixed in a 1 cm cuvette, and the bleaching was started by addition of hydrogen peroxide. The bleaching was detected spectrophotometrically at 610 nm, which is the absorption peak of this dye. Bleaching was followed for 10 minutes, and the bleaching rates (−ΔmAbs/min) were determined from the initial (linear) reduction in absorbance.

At pH 10.5 the bleaching using 100 nm CiP and ABTS as accelerator was so fast that bleaching was already completed before the cuvette could be placed in the spectrophotometer, the reason why the dosage of CiP at pH 10.5 was reduced to 1 nM when used in combination with ABTS, although a dosage near 100 nM CiP was necessary for all other (hitherto known) accelerators in order to see a significant reduction in absorbance.

Figure 4:
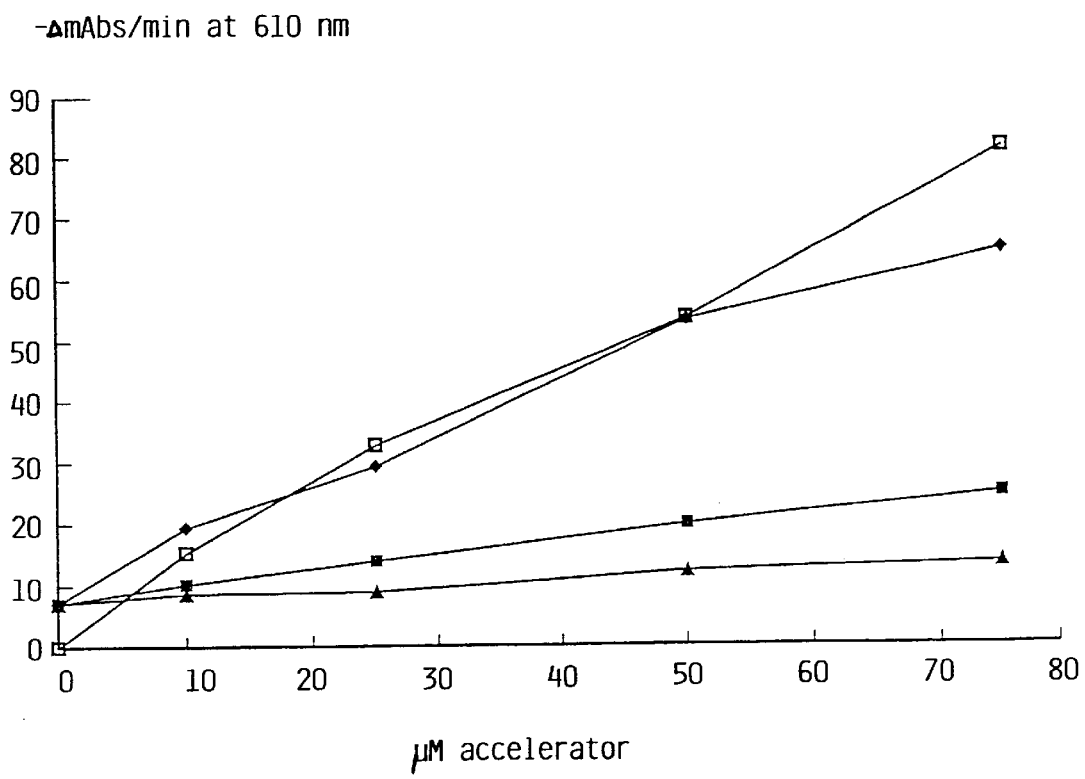
FIG. 4 shows a comparison of the initial bleaching rates during bleaching of Direct Blue 1 (DB1) at pH 10.5 (□ ABTS, 1 nM peroxidase; ♦ VAN, 100 nM peroxidase; ■ 7HCm, 100 nM peroxidase; ▲ pHBS, 100 nM peroxidase)
Figure 5:
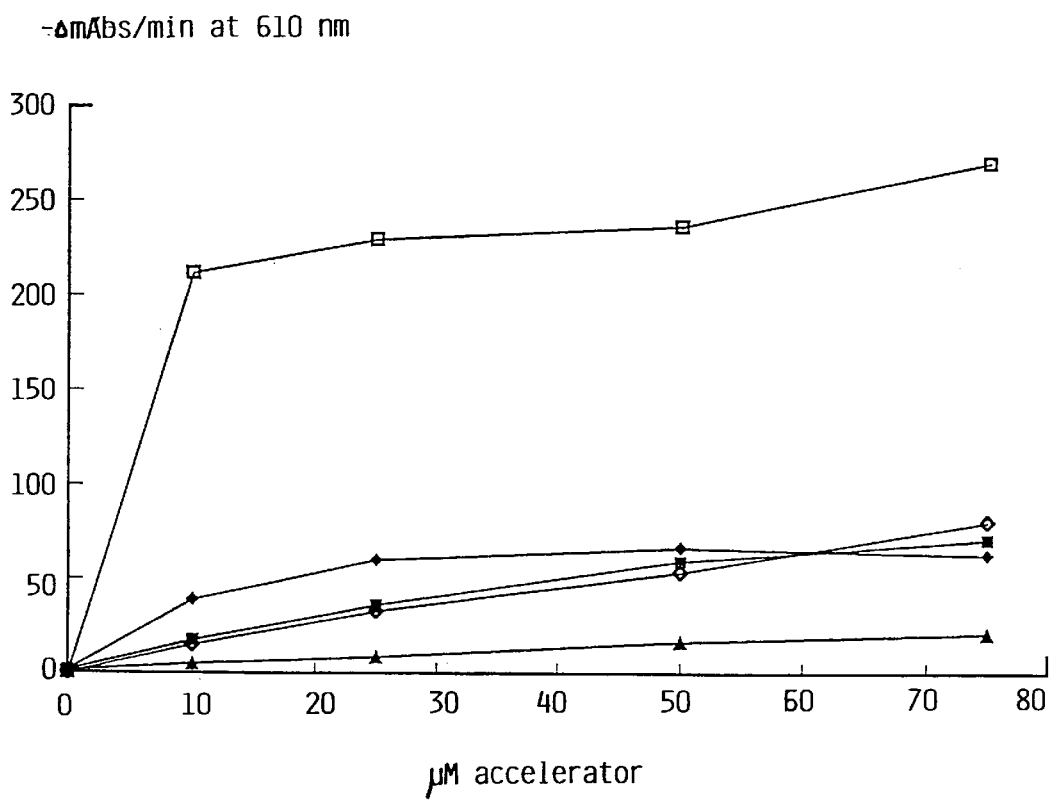
FIG. 5 shows a comparison of the initial bleaching rates during bleaching of DB1 at pH 8.8 (and pH 10.5) (□ ABTS pH 8.8; ♦ VAN pH 8.8; ■ 7HCm pH 8.8; ◊ ABTS pH 10.5; and ▲ pHBS pH 8.8).

The results of initial bleaching rate per minute have been illustrated in FIGS. 4 and 5 as function of accelerator concentration.

EXAMPLE 5

Enhanced Dye Transfer Inhibition by ABTS

A washing trial was carried out in a Terg-o-tometer to investigate the effect of ABTS on peroxidase based dye transfer inhibition. For a comparison, also the established enhancer pHBS was tested.

Clean white tracer test pieces (cotton, Style#400 from Testfabrics, Inc., U.S.A.; bleached, but unbrightened) were washed together with nylon test pieces dyed with the azo dye Acid Red 151 (C.I. 26900; available, e.g. from Aldrich Chemical Co.). Reference test pieces were cut out of the same cotton cloth and washed in the absence of dyed fabric. The dye transfer in a given Terg-o-tometer pot was measured as the Hunter colour difference $$\Delta E = \sqrt{(\Delta L)^2 + (\Delta a)^2 + (\Delta b)^2}$$

between the tracer pieces in that pot and the above reference pieces, the Hunter L, a, and b values being evaluated from remission data obtained with an unfiltered daylight source on a Datacolor Elrephometer 2000.

The detergent solution for the washing trial was made up using 4.5 g/l of a commercially available European high-pH powder detergent containing no bleach and no optical brightener. The water used was tap water mixed with demineralized water in the ratio 1:2; the mixture had a hardness equivalent to approx. 1.1 mM $Ca^{2+}$.

The detailed experimental conditions were:
Duration of wash: 15 min.
Terg-o-tometer agitation: 70 rotations/min.
Temperature: 35° C.
pH: Adjusted to 10.5 with NaOH prior to addition of peroxidase system
Textile load: Approx. 6 g nylon dyed with acid Red 151 and 1 g white cotton per liter washing liquor
Peroxide source: In all cases, 50 $\mu$M $H_2O_2$ was present together with the peroxidase
Peroxidase: *Coprinus cinereus* peroxidase obtained according to Example 1 at 5 nM After washing, the test pieces were rinsed thoroughly in cold tap water and dried in the dark overnight, after which the remission measurements were performed.

Treatments with various concentrations of the two enhancers yielded the following results:

| | Hunter ΔE with respect to white, washed fabric |
|---|---|
| 1 $\mu$M ABTS | 34.9 |
| 5 $\mu$M ABTS | 32.3 |
| 20 $\mu$M ABTS | 23.7 |
| 1 $\mu$M pHBS | 34.8 |
| 5 $\mu$M pHBS | 34.5 |
| 20 $\mu$M pHBS | 30.8 |

Differences of $\geq 2$ units of Hunter ΔE were statistically significant.

In both cases, the peroxidase system with 1 $\mu$M enhancer provided no significant dye transfer inhibition (reference without peroxidase system not included here). However, as is seen that the ABTS system has an effect already at 5 $\mu$M of enhancer, whereas the pHBS system does not; and at 20 $\mu$M enhancer, the ABTS system has a much larger effect than the pHBS system.

EXAMPLE 6

Bleaching of Direct Blue 1

A crude soy bean peroxidase (SBP) was purified by anion and cation chromatography followed by gelfiltration to a single protein on SDS-PAGE with an $R_2$-value ($A_{404nm}/A_{280nm}$) of 2.2:

125 ml of crude SBP were adjusted to pH 7, diluted to 2.3 mS and filtered through 0.8$\mu$ filter. The sample was applied to 300 ml of DEAE column equilibrated with 20 mM phosphate pH 7.0, and the peroxide was eluted with a 1 M NaCl linear gradient in the same buffer. Fractions with peroxidase activity were pooled.

Pooled fractions from anion exchange chromatography (190 ml) were concentrated and washed by ultrafiltration (GR61PP) membrane from Dow, Denmark). pH was adjusted to 5.3 ionic strength to 2.3 mS in the sample before application to a 200 ml S-Sepharose column previously equilibrated with 50 mM acetate pH 5.3. The effluent containing the peroxidase activity was concentrated and washed by ultrafiltration to a final volume of approx. 10 ml.

A 5 ml concentrated sample from cation exchange chromatography was applied to a 90 cm Sephacryl S-200 column equilibrated and eluted with 0.1 M acetate pH 6.1.

Fractions with peroxidase activity giving only one band on SDS-PAGE were pooled.

The bleaching rate of direct blue 1 (DB1) by the purified SBP was determined using a selection of enhancers according to the invention. The following conditions were used:

|  | Final concentration |
|---|---|
| 200 μl 50 mM Britton-Robinson buffer pH 6, 8 and 10, respectively | 10 mM |
| 200 μl DB1 ~ 3.0 Abs.Units (610 nm) | 0.6 ($A_{610nm}$) |
| 200 μl SBP with $A_{404nm}$ = 0.0005 at pH 6 and 8 or with $A_{404nm}$ = 0.005 at pH 10 | 0.0001 or 0.001 ($A_{404}$nm) |
| 200 μl 50 μM enhancer | 10 μM |
| 200 μl 100 μM $H_2O_2$ | 20 μM |

Reagents were mixed in a thermostated cuvette at 30° C. and the bleaching was started by addition of hydrogen peroxide.

The bleaching was detected and calculated as in Example 3.

From the results presented in Tables 2 and 3 below, it appears that by adding enhancers of the invention we can obtain a much faster bleaching of the dye compared to the experiments without enhancer.

TABLE 2

Bleaching of Direct Blue 1 with SBP in 4 Minutes

| | % DB1 bleaching in 4 min. | | |
|---|---|---|---|
| Enhancer | pH 6 | pH 8 | pH 10 10x[SBP] |
| No enhancer | 0.7 | <0.7 | <0.7 |
| 10-Phenothiazine propionic acid | 72 | 61 | 21 |
| 10-Ethyl-4-phenothiazine carboxylic acid | 69 | 69 | 32 |
| 10-Methylphenothiazine | 67 | 54 | 12 |
| 4'-Hydroxy-4-biphenyl-carboxylic acid | 61 | 47 | 10 |
| 10-Methylphenoxazine | 68 | 67 | 65 |
| pHBS | <0.7 | <0.7 | <0.7 |

TABLE 3

Initial Bleaching of Direct Blue 1 with SBP

| | (−ΔmAbs/min) | | |
|---|---|---|---|
| Enhancer | pH 6 | pH 8 | pH 10 10x[SBP] |
| No enhancer | <1 | <1 | <1 |
| 10-Phenothiazine propionic acid | 162 | 84 | 33 |
| 10-Ethyl-4-phenothiazine carboxylic acid | 228 | 120 | 45 |
| 10-Methylphenothiazine | 204 | 102 | 30 |
| 4'-Hydroxy-4-biphenyl-carboxylic acid | 237 | 132 | 9 |
| 10-Methylphenoxazine | 258 | 180 | 89 |
| pHBS | <1 | <1 | <1 |

EXAMPLE 7

Myxococcus virescens, DSM 8593, was inoculated on "5 CY" agar plates with the following composition:

| | |
|---|---|
| Casitone | 3 g |
| Yeast extract | 1 g |
| $CaCl_2.2H_2O$ | 1 g |
| Agar | 15 g |
| Water ad 1000 ml, pH 7.2 | | and incubated for 2 weeks at 26° C.

The agar was cut into pieces and transferred aseptically to 5 shake flasks with 100 ml "MD-1M"-medium in each flask.

The flasks were incubated on a rotary shaker at 250 rpm, 26° C., for 5 days. The combined culture from the 5 flasks was used for inoculating 50 flasks with 100 ml "MD-1M"-medium in each, using a 10 ml inoculum per flask.

The 50 flasks were incubated on a rotary shaker at 250 rpm, 26° C., for 3 days. The peroxidase activity as described above was measured in the combined culture from the 50 flasks, result: 0.2 PODU/ml.

After separation of the solid material by centrifugation the peroxidase was concentrated by ultrafiltration using a 10 kDa cut off membrane. The ultrafiltrated preparation had an activity of 2.9 PODU/ml.

The ultrafiltrated preparation described above was used in a dye bleaching experiment with Direct Blue 1 (DB1) at pH 10.5 (FIG. 6), with and without an enhancer of the invention, using the following conditions:

100 μM $H_2O_2$ 25 mM Borate pH 10.5

0.5 PODU/ml Myxococcus virescens peroxidase 0 or 10 μM 10-phenothiazinepropionic acid, respectively, room temperature the initial concentration of DB1 was adjusted to give an $OD_{610nm}$=0.6.

Reagents were mixed in a 1 cm cuvette, and the bleaching was started by addition of hydrogenperoxide. The bleaching was detected spectrophotometrically at 610 nm for 120 seconds.

Figure 6:
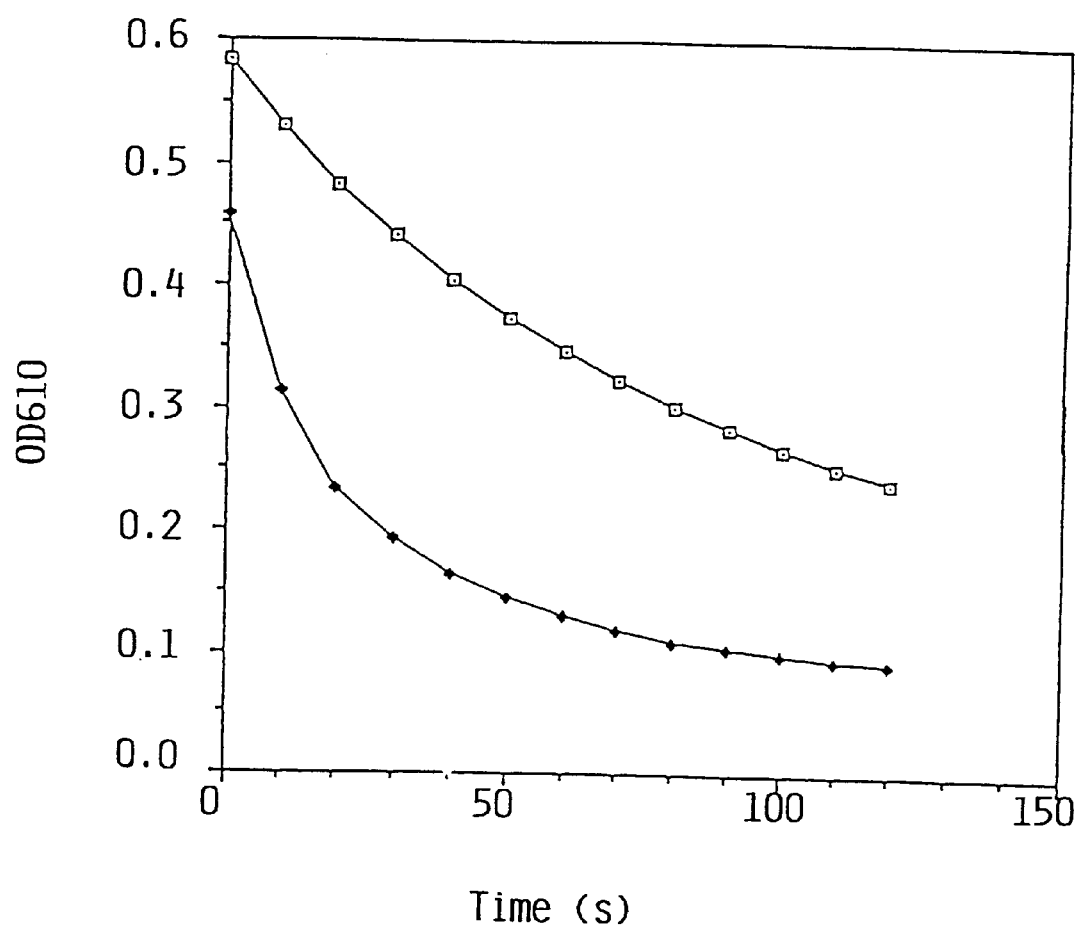
FIG. 6 shows the initial bleaching of DB1 at pH 10.5 under the following conditions: 100 μM $H_2O_2$; 25 mM Borate; 0.5 PODU/ml *Myxococcus virescens* peroxidase; 0 μM 10-propionic acid phenothiazine (□)/10 μM 10-propionic acid phenothiazine (♦), respectively; room temperature.

FIG. 6 shows that the effect of the enhancer is very pronounced. It also shows that the absorbance is reduced to at least half the initial value after 30 sec. in the experiment with 10 μM 10-propionic acid phenothiazine.

EXAMPLE 8

Bleaching of Direct Blue 1

Horse radish peroxidase type VI (HRPC) was obtained from Sigma (8P-8375).

The bleaching rate of direct blue 1 (DB1) by HRPC was determined using a selection of enhancers according to the invention. The following conditions were used:

|  | Final concentration |
|---|---|
| 200 µl 50 mM Britton-Robinson buffer pH 8 and 10, respectively | 10 mM |
| 200 µl DB1 ~ 3.0 Abs.Units (610 nm) | 0.6 ($A_{610nm}$) |
| 200 µl HRPC with $A_{404nm}$ = 0.005 | 0.001 ($A_{404nm}$) |
| 200 µl 50 µM enhancer | 10 µM |
| 200 µl 100 µM $H_2O_2$ | 20 µM |

Reagents were mixed in a thermostated cuvette at 30° C., and the bleaching was started by addition of hydrogen peroxide.

The bleaching was detected and calculated as in Example 3.

From the results presented in Table 4 below, it appears that by adding enhancers of the invention we can obtain a much faster bleaching of the dye compared to the experiment without enhancer.

TABLE 4

Initial Bleaching of Direct Blue 1 with HRPC

|  | −ΔmAbS/min | |
|---|---|---|
| Enhancer | pH 8 | pH 10 |
| No enhancer | <1 | <1 |
| 10-Phenothiazine propionic acid | 1061 | 62 |
| 10-Ethyl-4-phenothiazine carboxylic acid | 1038 | 68 |
| 10-Methylphenothiazine | 1164 | 83 |
| 10-Methylphenoxazine | 1188 | 99 |
| pHBS | <2 | <2 |

We claim:
1. A detergent composition comprising
(a) a surfactant,
(b) an enzyme exhibiting peroxidase activity,
(c) one or more other enzymes selected from the group consisting of protease, lipase, amylase, cellulase and oxidase, and
(d) an enhancing agent of formula I

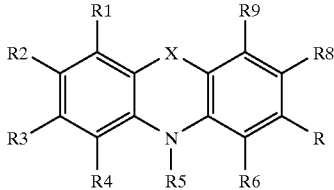

(I)

wherein
X is —O— or —S—;
R$^1$–R$^9$ independently are hydrogen, halogen, hydroxy, formyl, carboxy or an ester or salt thereof, carbamoyl, sulfo or an ester or salt thereof, sulfamoyl, phospho, phosphono, phosphonooxy or an ester or salt thereof, amino, phenyl, C$_1$–C$_{14}$-alkyl, C$_1$–C$_5$-alkoxy, carbonyl-C$_1$–C$_5$-alkyl, aryl-C$_1$–C$_5$-alkyl; wherein the carbamoyl, sulfamoyl, and amino are unsubstituted or substituted once or twice with R$^{10}$; the phenyl is unsubstituted or substituted with one or more R$^{10}$; and the C$_1$–C$_{14}$-alkyl, C$_1$–C$_5$-alkoxy, carbonyl-C$_1$–C$_5$-alkyl, and aryl-C$_1$–C$_5$-alkyl are saturated or unsaturated, branched or unbranched, and unsubstituted or substituted with one or more R$^{10}$; wherein R$^{10}$ is halogen, hydroxy, formyl, carboxy or an ester or salt thereof, carbamoyl, sulfo or an ester or salt thereof, sulfamoyl, phospho, phosphono, phosphonooxy or an ester or salt thereof, nitro, amino, phenyl, aminoalkyl, piperidino, piperazinyl, pyrrolidino, C$_1$–C$_5$-alkyl, C$_1$–C$_5$-alkoxy; wherein the carbamoyl, sulfamoyl, and amino are unsubstituted or substituted once or twice with hydroxy, C$_1$–C$_5$-alkyl, C$_1$–C$_5$-alkoxy; wherein the phenyl may be substituted with one or more of halogen, hydroxy, amino, formyl, carboxy or an ester or salt thereof, carbamoyl, sulfo or an ester or salt thereof, and sulfamoyl; and wherein the C$_1$–C$_5$-alkyl and C$_1$–C$_5$-alkoxy are saturated or unsaturated, branched or unbranched, and may be substituted once or twice with any of halogen, hydroxy, amino, formyl, carboxy or an ester or salt thereof, carbamoyl, sulfo or an ester or salt thereof, and sulfamoyl; or
two of the substituent groups R$^1$–R$^8$ together form a group —B—, wherein B is (—CHR$^{10}$—N=N—), (—CH=CH—)$_n$, (—CH=N—)$_n$ or (—N=CR$^{10}$—NR$^{10}$—) wherein n is 1, 2 or 3.

2. The detergent composition of claim 1, wherein X is —O—.

3. The detergent composition of claim 1, wherein X is —S—.

4. The detergent composition of claim 2, wherein R$^1$–R$^9$ are independently hydrogen, halogen, hydroxy, amino, phenyl, C$_1$–C$_{14}$-alkyl, C$_1$–C$_5$-alkoxy, wherein the C$_1$–C$_{14}$-alkyl and C$_1$–C$_5$-alkoxy are unsubstituted, saturated or unsaturated, branched or unbranched.

5. The detergent composition of claim 3, wherein R$^1$–R$^9$ are independently hydrogen, halogen, hydroxy, amino, phenyl, C$_1$–C$_{14}$-alkyl, C$_1$–C$_5$-alkoxy, wherein the C$_1$–C$_{14}$-alkyl and C$_1$–C$_5$-alkoxy are unsubstituted, saturated or unsaturated, branched or unbranched.

6. The detergent composition of claim 2, wherein R$^5$ is an alkyl group which is unsubstituted or substituted with one or more R$^{10}$.

7. The detergent composition of claim 3, wherein R$^5$ is an alkyl group which is unsubstituted or substituted with one or more R$^{10}$.

8. The detergent composition of claim 4, wherein R$^5$ is an alkyl group which is unsubstituted or substituted with one or more R$^{10}$.

9. The detergent composition of claim 5, wherein R$^5$ is an alkyl group which is unsubstituted or substituted with one or more R$^{10}$.

10. The detergent composition of claim 1, wherein the enhancing agent is 10-methylphenothiazine, 10-phenothiazine-propionic acid, N-hydroxysuccinimide-10-phenothiazine-propionate, 10-ethyl-4-phenothiazine-carboxylic acid, 10-ethylphenothiazine, 10-propylphenothiazine, 10-isopropylphenothiazine, methyl-10-phenothiazinepropionate, 10-phenylphenothiazine, 10-allylphenothiazine, 10-(3-(4-methyl-1-piperazinyl)propyl)phenothiazine, 10-(2-pyrrolidinoethyl)phenothiazine, 2-chloro-10-methylphenothiazine, 2-acetyl-10-methylphenothiazine, 4-carboxy-10-phenothiazine-propionic acid or chlorpromazine.

11. The detergent composition of claim 1, wherein the enhancing agent is 10-methylphenoxazine, 10-ethylphenoxazine, 10-phenoxazine-propionic acid or 4-carboxy-10-phenoxazine-propionic acid.

12. The detergent composition of claim 1, wherein the enzyme exhibiting peroxidase activity is horseradish peroxidase, soy bean peroxidase or a peroxidase derived from Coprinus, Bacillus, or Myxococcus.

13. The detergent composition of claim 1, wherein the amount of the enhancing agent is in the range of from 0.01–500 μM.

14. The detergent composition of claim 1 which has a pH in the range of from 7–13.

15. The detergent composition of claim 14 which has a pH in the range of from 7–11.

16. The detergent composition of claim 14 which has a pH in the range of from 8–12.

17. The detergent composition of claim 15 which has a pH in the range of from 8–11.

18. A method of washing a fabric, comprising treating the fabric with
(a) a surfactant,
(b) an enzyme exhibiting peroxidase activity, and
(c) one or more other enzymes selected from the group consisting of protease, lipase, amylase, cellulase and oxidase, and (d) an enhancing agent of formula I:

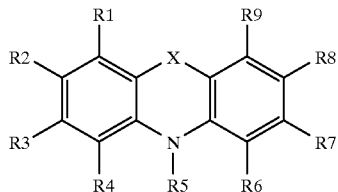

(I)

wherein

X is —O— or —S—;

$R^1$–$R^9$ independently are hydrogen, halogen, hydroxy, formyl, carboxy or an ester or salt thereof, carbamoyl, sulfo or an ester or salt thereof, sulfamoyl, phospho, phosphono, phosphonooxy or an ester or salt thereof, amino, phenyl, $C_1$–$C_{14}$-alkyl, $C_1$–$C_5$-alkoxy, carbonyl-$C_1$–$C_5$-alkyl, aryl-$C_1$–$C_5$-alkyl; wherein the carbamoyl, sulfamoyl, and amino are unsubstituted or substituted once or twice with $R^{10}$; the phenyl is unsubstituted or substituted with one or more $R^{10}$; and the $C_1$–$C_{14}$-alkyl, $C_1$–$C_5$-alkoxy, carbonyl-$C_1$–$C_5$-alkyl, and aryl-$C_1$–$C_5$-alkyl are saturated or unsaturated, branched or unbranched, and unsubstituted or substituted with one or more $R_{10}$; wherein $R_{10}$ is halogen, hydroxy, formyl, carboxy or an ester or salt thereof, carbamoyl, sulfo or an ester or salt thereof, sulfamoyl, phospho, phosphono, phosphonooxy or an ester or salt thereof, nitro, amino, phenyl, aminoalkyl, piperidino, piperazinyl, pyrrolidino, $C_1$–$C_5$-alkyl, $C_1$–$C_5$-alkoxy; wherein the carbamoyl, sulfamoyl, and amino are unsubstituted or substituted once or twice with hydroxy, $C_1$–$C_5$-alkyl, $C_1$–$C_5$-alkoxy; wherein the phenyl may be substituted with one or more of halogen, hydroxy, amino, formyl, carboxy or an ester or salt thereof, carbamoyl, sulfo or an ester or salt thereof, and sulfamoyl; and wherein the $C_1$–$C_5$-alkyl and $C_1$–$C_5$-alkoxy are saturated or unsaturated, branched or unbranched, and may be substituted once or twice with any of halogen, hydroxy, amino, formyl, carboxy or an ester or salt thereof, carbamoyl, sulfo or an ester or salt thereof, and sulfamoyl; or two of the substituent groups $R^1$–$R^8$ together form a group —B—, wherein B is (—CHR$^{10}$—N=N—), (—CH=CH—)$_n$, (—CH=N—)$_n$ or (—N =CR$^{10}$—NR$^{10}$—) wherein n is 1, 2 or 3.

19. The method of claim 18, wherein X is —O—.

20. The method of claim 18, wherein X is —S—.

21. The method of claim 19, wherein $R^1$–$R^9$ are independently hydrogen, halogen, hydroxy, amino, phenyl, $C_1$–$C_{14}$-alkyl, $C_1$–$C_5$-alkoxy, wherein the $C_1$–$C_{14}$-alkyl and $C_1$–$C_5$-alkoxy are unsubstituted, saturated or unsaturated, branched or unbranched.

22. The method of claim 20, wherein $R^1$–$R^9$ are independently hydrogen, halogen, hydroxy, amino, phenyl, $C_1$–$C_{14}$-alkyl, $C_1$–$C_5$-alkoxy, wherein the $C_1$–$C_{14}$-alkyl and $C_1$–$C_5$-alkoxy are unsubstituted, saturated or unsaturated, branched or unbranched.

23. The method of claim 19, wherein $R^5$ is an alkyl group which is unsubstituted or substituted with one or more $R^{10}$.

24. The method of claim 20, wherein $R^5$ is an alkyl group which is unsubstituted or substituted with one or more $R^{10}$.

25. The method of claim 21, wherein $R^5$ is an alkyl group which is unsubstituted or substituted with one or more $R^{10}$.

26. The method of claim 22, wherein $R^5$ is an alkyl group which is unsubstituted or substituted with one or more $R^{10}$.

27. The method of claim 18, wherein the enhancing agent is 10-methylphenothiazine, 10-phenothiazine-propionic acid, N-hydroxysuccinimide-10-phenothiazine-propionate, 10-ethyl-4-phenothiazine-carboxylic acid, 10-ethylphenothiazine, 10-propylphenothiazine, 10-isopropylphenothiazine, methyl-10-phenothiazinepropionate, 10-phenylphenothiazine, 10-allylphenothiazine, 10-(3-(4-methyl-1-piperazinyl) propyl)phenothiazine, 10-(2-pyrrolidinoethyl) phenothiazine, 2-chloro-10-methylphenothiazine, 2-acetyl-10-methylphenothiazine, 4-carboxy-10-phenothiazine-propionic acid or chlorpromazine.

28. The method of claim 18, wherein the enhancing agent is 10-methylphenoxazine, 10-ethylphenoxazine, 10-phenoxazine-propionic acid or 4-carboxy-10-phenoxazine-propionic acid.

29. The method of claim 18, wherein the enzyme exhibiting peroxidase activity is horseradish peroxidase, soy bean peroxidase or a peroxidase derived from Coprinus, Bacillus, or Myxococcus.

30. The method of claim 18, wherein the amount of the enhancing agent is in the range of from 0.01–500 μM.

31. The method of claim 18, wherein the fabric is treated at a pH in the range of from 7–13.

32. The method of claim 31 which the fabric is treated at a pH in the range of from 7–11.

33. The method of claim 31 which the fabric is treated at a pH in the range of from 8–12.

34. The method of claim 32 which the fabric is treated at a pH in the range of from 8–11.

* * * * *